US006673341B2

(12) United States Patent
Sukhatme

(10) Patent No.: US 6,673,341 B2
(45) Date of Patent: Jan. 6, 2004

(54) METHODS OF INHIBITING PROLIFERATIVE DISEASES BY INHIBITING TGF-β-MEDIATED ANGIOGENESIS

(75) Inventor: Vikas P. Sukhatme, Newton Center, MA (US)

(73) Assignee: Beth Israel Deaconness Medical Center

(*) Notice: Subject to any disclaimer, the term of this patent is extended or adjusted under 35 U.S.C. 154(b) by 0 days.

(21) Appl. No.: 09/346,179

(22) Filed: Jul. 1, 1999

(65) Prior Publication Data

US 2002/0193326 A1 Dec. 19, 2002

Related U.S. Application Data

(60) Provisional application No. 60/091,829, filed on Jul. 6, 1998.

(51) Int. Cl.$^7$ .............................................. A61K 39/395

(52) U.S. Cl. .............................. 424/130.1; 424/145.1; 424/138.1

(58) Field of Search ..................... 435/7.1, 7.2, 7.23; 436/64; 530/387.7, 387.9, 388.8; 424/130.1, 145.1, 138.1

(56) References Cited

U.S. PATENT DOCUMENTS

| 5,571,714 A | 11/1996 | Dasch et al. ........... 435/240.27 |
| 5,639,725 A | * 6/1997 | O'Reilly et al. |
| 5,854,205 A | * 12/1998 | O'Reilly et al. |

FOREIGN PATENT DOCUMENTS

| GB | 2 305 921 A | 4/1997 |
| WO | WO 92/00330 | 1/1992 |
| WO | WO 97/13844 | 4/1997 |

OTHER PUBLICATIONS

Linehan et al. ("Cancers of the Genitourinary System", Cancers: Principles and Practices of Oncology, 6th edition, 2001, Lippincott Williams &Wilkins, pp. 1343–1344).*
Teicher et al. (Cancer Research, vol. 52, No. 23, 1992, abstract only).*
Baldwin et al, Monoclonal Antibodies for Cancer Detection and Therapy, 1985: p. 20.*
Ananth, S., et al., "Transforming Growth Factor β1. Is a Target for the von Hippel–Lindau Tumor Suppressor and a Critical Growth Factor for Clear Cell Renal Carcinoma," *Cancer Research* 59:2210–2216 (1999).
Arteaga, C.L., et al., "Anti–Transforming Growth Factor (TGF)—βAntibodies Inhibit Breast Cancer Cell Tumorigenicity and Increase Mouse Spleen Natural Killer Cell Activity—Implications for a Possible Role of Tumor Cell/Host TGF–β Interactions in Human Breast Cancer Progresssion," *J. Clin. Invest.* 92:2569–2576 (1993).

Filmus, J. and Kerbel, R.S., "Development of resistance mechanisms to the growth–inhibitory effects of transforming growth factor–β during tumor progression," *Current Opinion in Oncology* 5:123–129 (1993).
Goggins, M., et al., "Genetic Alterations of the Transforming Growth Factor β Receptor Genes in Pancreatic and Biliary Adenocarcinomas," *Cancer Research* 58:5329–5332 (1998).
Gomella, L.G., et al., "Expression of Transforming Growth Factor α in Normal Human Adult Kidney and Enhanced Expression of Transforming Growth Factors α and β1 in Renal Cell Carcinoma," *Cancer Research* 49:6972–6975 (1989).
Huang, F., et al., "Transforming Growth Factor β1 (TGFβ1) is an Autocrine Positive Regulator of Colon Carcinoma U9 Cells in Vivo as Shown by Transfection of a TGFβ1 Antisense Expression Plasmid," *Cell Growth & Differentiation* 6:1635–1642 (1995).
Huang, S.S., et al., "Transforming Growth Factor β Peptide Antagonists and Their Conversion to Partial Agonists," *The Journal of Biological Chemistry* 272(43):27155–27159 (1997).
Ivanovic, V., et al., "Elevated Plasma levels of TGF–β1 in patients with invasive prostate cancer," *Nature Medicine* 1(4):282–283 (1995).
Knebelmann, B., et al., "Transforming Growth Factor α Is a Target for the Von Hippel–Lindau Tumor Suppressor," *Cancer Research* 58:226–231 (1998).
Markowitz, S., et al., "Inactivation of the Type II TGF–β Receptor in Colon Cancer Cells with Microsatellite Instability," *Science* 268:1336–1338 (1995).
Mauceri, H.J., et al., "Combined effects of angiostatin and ionizing radiation in antitumour therapy," *Nature* 394:287–291 (1998).
Norgaard, P., et al., "Transforming growth factor β and cancer," *Cancer Treatment Reviews* 21:367–403 (1995).
Pepper, M.S., et al., "Angiogenesis–Regulating Cytokines: Activities and Interactions," *Curr. Topics Microbiol. Immunol.* 213:31–67 (1996).
Tzai, T.–S., et al., "Modulation of the Immunostimulating Effect of Autologous Tumor Vaccine by Anti–TGF–β Antibody and Interferon–α on Murine MBT–2 Bladder Cancer," *Anticancer Research* 17:1073–1078 (1997).
Yang, Y., et al., "Role of Carbohydrate Structures in the Binding of β1–Latency–Asscociated Peptide to Ligands," *Biochemistry* 36:11923–11932 (1997).
Ueki, N., et al., "Excessive production of transforming growth–factor β1 can play an important role in the development of tumorigenesis by its action for angiogenesis: validity of neutralizing antibodies to block tumor growth," *Biochimica et Biophysica Acta* 1137:189–196 (1992).

(List continued on next page.)

Primary Examiner—Anthony C. Caputa
Assistant Examiner—Gary B Nickol
(74) Attorney, Agent, or Firm—Palmer & Dodge, LLP; Barbara A. Gyure; Kathleen M. Williams

(57) ABSTRACT

Disclosed are methods of inhibiting proliferative diseases characterized by TGF-β-mediated angiogenesis.

1 Claim, 9 Drawing Sheets

OTHER PUBLICATIONS

Stiles, J. D., et al., "Correlation of Endothelin–1 and Transforming Growth Factor β1 with Malignancy and Vascularity in Human Gliomas," Journal of Neuropathology and Experimental Neurology 56(4) : 435–439 (Apr. 1997).

Marzo, A.L., et al., "Antisense Oligonucleotides Specific for Transforming Growth Factor β2 Inhibit the Growth of Malignant Mesothelioma Both in Vitro and in Vivo[1]," Cancer Research 57 (15) :3200–3207 (Aug. 1, 1997).

* cited by examiner

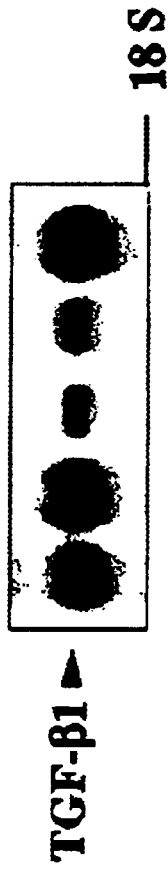

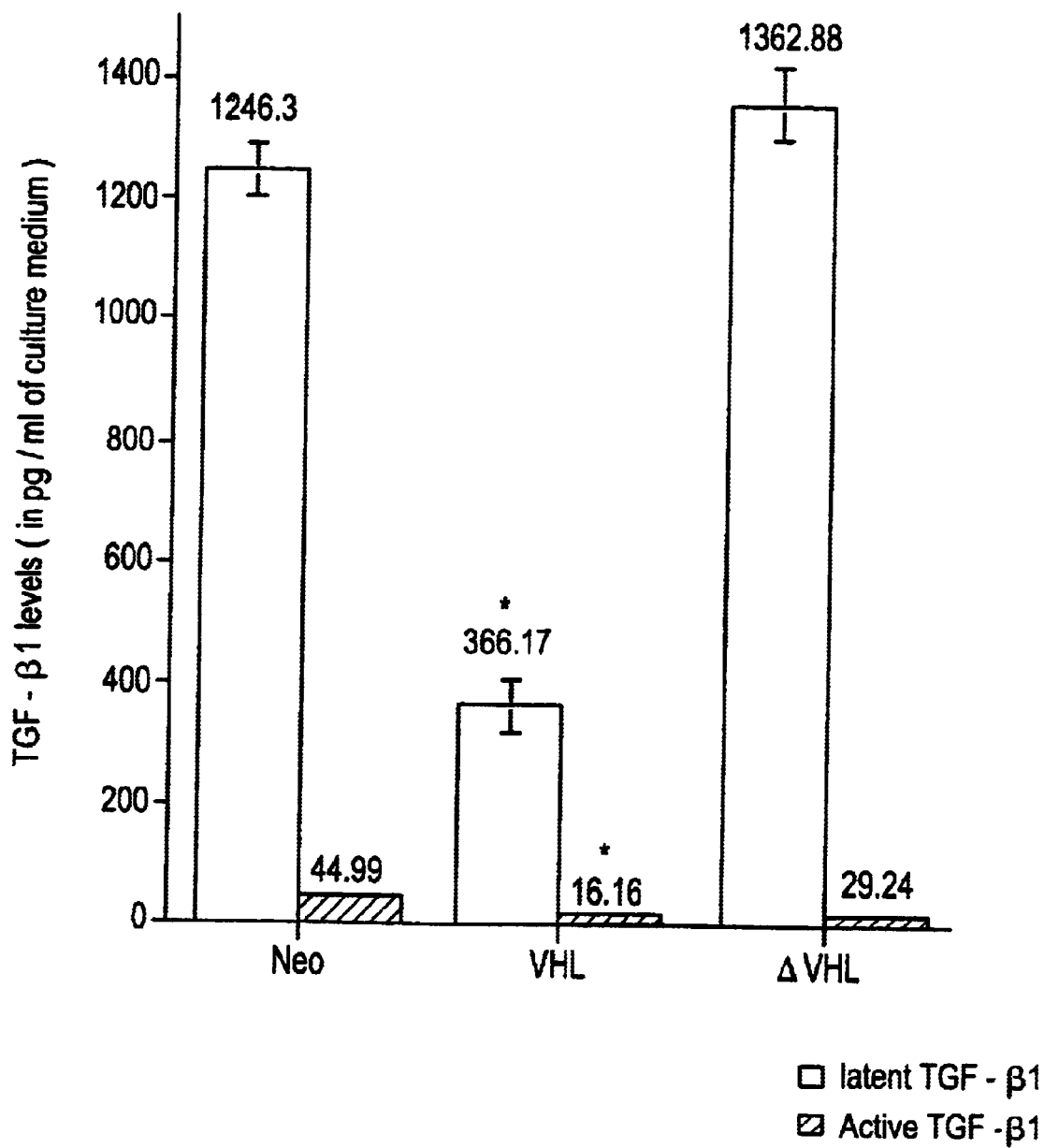

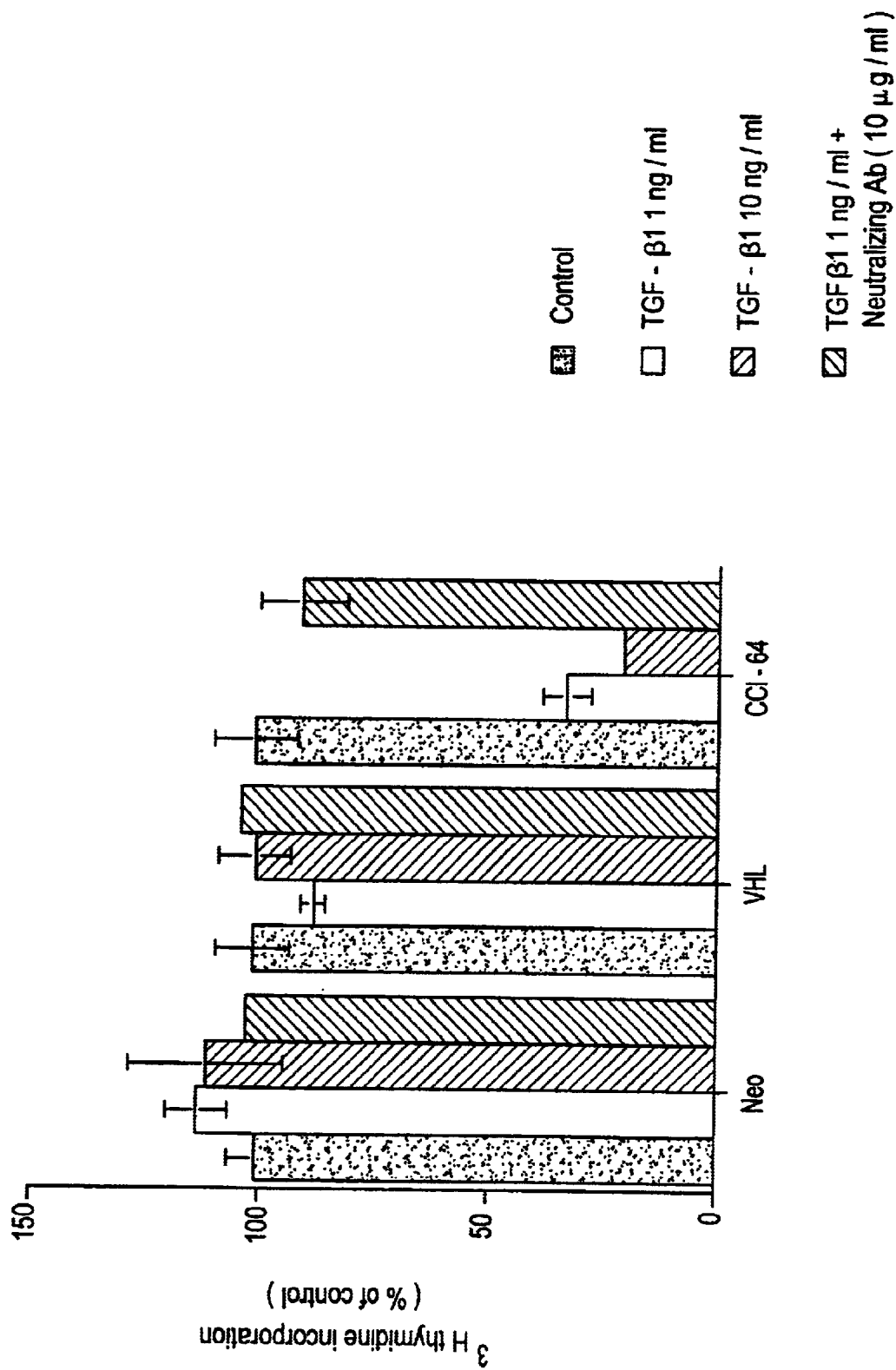

METHODS OF INHIBITING PROLIFERATIVE DISEASES BY INHIBITING TGF-β-MEDIATED ANGIOGENESIS

RELATED APPLICATION

This application claims benefit to provisional application No. 60/091,829, filed Jul. 6, 1998, now abandoned, the entire teachings of which are incorporated herein by reference.

GOVERNMENT SUPPORT

The invention was supported, in whole or in part, by a NIH R01 grant from National Institutes of Health. The Government has certain rights in the invention.

BACKGROUND OF THE INVENTION

TGF-β1 is a polypeptide growth factor that belongs to a large family of structurally related growth factors referred to as the TGF-β superfamily. It is a multifunctional cytokine that plays a major role in morphogenesis, development, tissue repair, and in the pathogenesis of fibrotic diseases (Massague, J. et al., *Cancer Surv* 1992;12:81–103 (1992), Norgaard, P., Hougaard, S., Poulsen, H. S. & Spang-Thomsen, M., *Cancer Treat Rev* 21, 367–403 (1995)). While TGF-β1 was originally described as an inducer of anchorage independent growth in fibroblasts, it is known to be a potent inhibitor of epithelial cell growth, though it can stimulate the growth of certain tumor cells (Huang, F., Newman, E., Theodorescu, D., Kerbel, R. S. & Friedman, E., *Cell Growth Differ* 6, 1635–1642 (1995), Lu, C. & Kerbel, R. S., *Curr Opin Oncol* 6, 212–220 (1994)). The role of TGF-β in human malignancies is complex and both paracrine and autocrine actions need to be assessed. TGF-β1 is elevated in several cancers including clear-cell renal carcinomas (RCCs) (Derynck, R. et al., *Cancer Res* 4 7, 707–712 (1987), Gomella, L. G. et al., *Cancer Res* 49, 6972–6975 (1989), Ramp, U. et al., *J Urol* 157, 2345–2350 (1997)). Some tumor cells are sensitive to TGF-β's growth suppressive effects, whereas others are not (Gomella, L. G. et al., *Cancer Res* 49, 6972–6975 (1989), MacKay, S. L. et al., *Ann Surg* 2 2 1, 767–776; discussion 776–767 (1995), Jakowlew, S. B., Mathias, A., Chung, P. & Moody, T. W., *Cell Growth Differ* 6, 465–476 (1995), Jakowlew, S. B., Moody, T. W. & Mariano, J. M., *Anticancer Res* 17, 1849–1860 (1997), and Norgaard, P., Spang-Thomsen, M. & Poulsen, H. S., *Br J Cancer* 73, 1037–1043 (1996)). In a recent paper, 20/20 primary RCCs and 30/30 RCC cell lines expressed TGF-β1, with the majority of the cell lines resistant to the growth suppressive effect of exogenous TGF-β1 (Ramp, U. et al, *Lab Invest* 76, 739–749 (1997)). Moreover, serum and urine levels of TGF-β1 and tissue expression of TGF-β1 mRNA in several cancers correlate inversely with prognosis, suggesting an important paracrine role for TGF-β1 in promoting tumor progression and possibly metastasis in vivo (Tsai, J. F. et al., *Medicine* (Baltimore) 76, 213–226 (1997), Knoefel, B. et al., *J Interferon Cytokine Res* 17, 95–102 (1997), Ivanovic, V., Melman, A., Davis-Joseph, B., Valcic, M. & Gellebter, J., *Nat Med* 1, 282–284 (1995), Friess, H. et al., *Gastroenterology* 105, 1846–1856 (1993), and Junker, U. et al., *Cytokine* 8, 794–798 (1996)).

RCC is the most common cancer of the kidney, occurring in over 27,000 individuals in the U.S. each year and is responsible for over 11,000 deaths annually (Linehan, W. M., Lerman, M. I. & Zbar, B., *JAMA* 273, 564–570 (1995)). The treatment of RCC remains frustrating to the oncologist; locally unresectable and metastatic disease has dismal prognosis. There is tremendous need to understand the basic biology of RCC and develop better therapeutic options. Most sporadic and hereditary RCCs (VHL-disease associated) have mutated and/or loss of both copies of the VHL gene (Linehan, W. M., Lerman, M. I. & Zbar, B., *JAMA* 273, 564–570 (1995)). The VHL gene product (pVHL) is lost in early atypical cysts, suggesting that pVHL might play a "gatekeeper" role in RCC development, analogous to the APC gene product in colon cancer (Lubensky, I. A. et al., *J Pathol* 149, 2089–2094 (1996) and Maher, E. R. & Kaelin, W. G., Jr., *Medicine* (Baltimore) 76, 381–391 (1997)). VHL-disease associated tumors are typically hypervascular and target genes identified to date include VEGF, TGF-α and PDGF-B, all of which have pro-angiogenic effects (Iliopoulos, O., Levy, A. P., Jiang, C., Kaelin, W. G., Jr. & Goldberg, M. A., *Proc Natl Acad Sci USA* 93, 10595–10599 (1996), Knebelmann, B., Ananth, S., Cohen, H. T. & Sukhatme, V. P., *Cancer Res* 58, 226–231 (1998), Mukhopadhyay, D., Knebelmann, B., Cohen, H. T., Ananth, S. & Sukhatme, V. P., *Mol Cell Biol* 17, 5629–5639 (1997), and Gnarra, J. R. et al., *Proc Natl Acad Sci USA* 93, 10589–10594 (1996)). TGF-β is another gene significantly involved in angiogenesis (Pepper, M. S., Mandriota, S. J., Vassalli, J. D., Orci, L. & Montesano, R., *Curr Top Microbiol Immunol* 213, 31–67 (1996)). Although TGF-β1 has been found to be elevated in RCCs (Derynck, R. et al., *Cancer Res* 47, 707–712 (1987), Gomella, L. G. et al., *Cancer Res* 49, 6972–6975 (1989), Ramp, U. et al., *J Urol* 157, 2345–2350 (1997), Ramp, U. et al., *Lab Invest* 76, 739–749 (1997), and Knoefel, B. et al., *J Interferon Cytokine Res* 17, 95–102 (1997)) there has been no link to date with the VHL tumor suppressor and no functional role has been ascribed to TGF-β1 for RCC growth in vivo.

SUMMARY OF THE INVENTION

The present invention is based on the discovery that TGF-β1 is a novel target gene for pVHL (von Hippel-Lindau) and that pVHL regulates the TGF-β1 gene at the post-transcriptional level. Furthermore, as described herein, evidence is presented that antagonizing the effects of TGF-β1 suppresses tumor growth in vivo through an anti-angiogenic mechanism.

In particular, the present invention relates to methods of inhibiting proliferative diseases in a vertebrate. The proliferative disease is characterized as having increased production of TGF-β and is further characterized by having angiogenic activity. The increased TGF-β production can be global, or be very localized, and the TGF-β can be secreted either by proliferating cells, or by stromal cells, such as fibroblasts, macrophages, platelets, endothelial calls, granular neutrophils, and other cells. Because TGF-β can auto-regulate itself, and induce production of more TGF-β, the cells surrounding those producing TGF-β can in turn produce TGF-β. More particularly, the angiogenic activity is TGF-β-mediated angiogenic activity and the inhibition of the proliferative disease results from the inhibition of TGF-β-mediated angiogenesis, specifically the "resolution" phase of TGF-β-mediated angiogenesis. As defined herein, the "resolution" phase of angiogenesis is the phase of angiogenesis where endothelial cells stop proliferating and migrating, in which basement membrane reforms and in which pericytes, the differentiation of which is known to be TGF-β dependent, attach to the basement membrane.

Although any proliferative disease characterized as above is encompassed by the present invention, in one embodiment of the present invention, the proliferative disease is cancer, or tumor growth, and the inhibition of the disease results in inhibiting the growth of a tumor, or in the regression of an already established tumor. In particular, the cancer is clear-cell renal carcinoma, or RCC.

As described herein, TGF-β-mediated angiogenesis can be inhibited by contacting the proliferating cells with a molecule that inhibits (or neutralizes or antagonizes) angiogenic activity mediated by TGF-β, including TGF-β1, TGF-β2, and TGF-β3. For example, the molecule can be an anti-TGF-β antibody, a TGF-β antagonist such as decorin or LAP, a soluble form of a TGF-β receptor or an anti-sense oligonucleotide that binds to (hybridizes with) DNA or RNA encoding TGF-β, or molecules that block TGF-β's interaction with receptor(s), molecules working intracellularly, i.e., downstream, of TGF-β receptor(s).

In another embodiment of the present invention, the proliferative disease is inhibited by contacting the proliferating cells with a molecule that inhibits TGF-β activity as described above in combination with one, or more additional anti-angiogenic molecules, e.g., angiostatin or endostatin or restin, or biologically active fragments thereof. In yet another embodiment of the present invention, the proliferating cells are contacted with a chemotherapeutic, immunotherapeutic or radiologic agent in combination with the molecule that inhibits TGF-β angiogenic activity. Additionally encompassed by the present invention is any combination therapy including of molecules that inhibit TGF-β-mediated angiogenic activity, other anti-angiogenic molecules, chemotherapy, immunotherapy and/or radiation therapy.

Also encompassed by the present invention is a method of monitoring tumor growth or cancer progression in a vertebrate. In one embodiment of the present invention, tumor metastases in a mammal is monitored by evaluating (e.g., determining) TGF-β levels in a biological sample obtained from the mammal considered to be at risk for tumor metastases.

In another embodiment of the present invention, the efficacy of an anti-tumor therapy is evaluated where cells obtained from the tumor are evaluated for the expression of functional TGF-β receptors. As defined herein, a functional (e.g., biologically active) TGF-β receptor is a receptor that binds TGF-β, or a fragment thereof. If the proliferating cells express functional TGF-β receptors, then the anti-tumor therapy can include contacting the tumor cells with TGF-β, or a biologically active fragment thereof. As defined herein, the biological activity of TGF-β includes any of the known cytokine activities of TGF-β, including the ability to bind to its cognate receptor, inhibit epithelial cell growth and/or differentiation, as well as the ability to specifically bind to anti-TGF-β antibodies or to stimulate immunogenic response (e.g., elicit antibodies) in a mammal. If the proliferating cells do not express functional TGF-β receptors, or do not express TGF-β receptors at all, then the choice of therapy would include contacting the tumor cells with a molecule that inhibits TGF-β-mediated angiogenic activity.

Thus, as described herein, for the first time, TGF-β is shown to be a target for the VHL (von Hippel-Lindau) tumor suppressor and a critical growth factor for clear-cell renal carcinoma. Additionally, as described herein, antagonizing TGF-β activity (in particular its paracrine activity) provides novel methods of inhibiting proliferating cells that secrete TGF-β, or by inhibiting proliferating cells that cause the secretion of TGF-β by stromal cells, and more specifically, by TGF-β-secreting tumors such as clear-cell renal carcinoma.

BRIEF DESCRIPTION OF THE DRAWINGS

FIG. 1A is a photograph showing the results of an experiment of VHL transfection of 786-0 cells significantly repressed TGF-β1 message (about 2.5 kb). Fold inhibition was calculated by densitometry using actin as a normalization control.

FIG. 1B is a photograph showing the results of an experiment confirming expression of HA-tagged and Flag-tagged pVHL and pΔVHL by Western analysis using a monoclonal VHL antibody. Each lane contains 20 μg of whole cell lysate from stably transfected 786-0 cells indicated in FIG. 1A.

FIG. 1C is a graph showing the results of an experiment where a 3–4 fold downregulation of latent and active TGF-β1 protein in the supernatant of cells transfected with VHL. Results are expressed as mean+/–S.E of 3 independent experiments and were statistically significant (p<0.01 using ANOVA).

FIG. 3A is a graph showing the results of an experiment demonstrating the lack of growth responsiveness of RCC cells to exogenous TGF-β1: The effect of TGF-β1 on DNA synthesis is shown for 786-0 Neo and 786-VHL cells. Mink lung epithelial cells (CCL-64) which are growth suppressed by TGF-β1 were used as a positive control.

DETAILED DESCRIPTION OF THE INVENTION

Figure 2A:
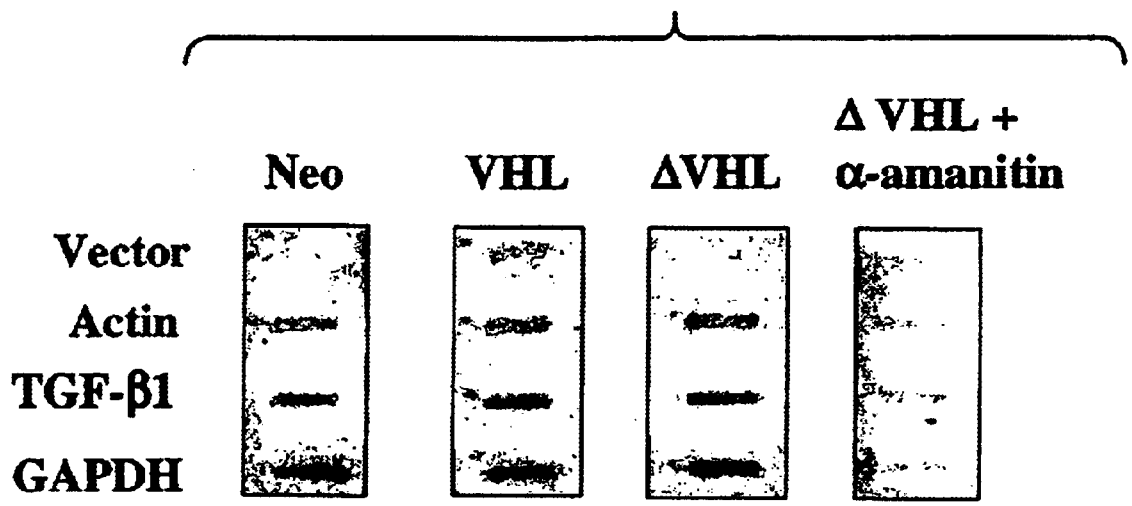
FIG. 2A is an autoradiogram showing the results of an experiment demonstrating that pVHL does not modify the transcription rate of TGF-β1 gene.

The human VHL gene encodes a 213 amino acid protein and is expressed in all tissues. VEGF, PDGF and GLUT-1 were the first target genes identified for pVHL. Recently it has been found that TGF-α is another target gene for pVHL (Knebelmann, B., Ananth, S., Cohen, H. T. & Sukhatme, V. P., *Cancer Res* 58, 226–231 (1998)). As described herein, both TG-β1 mRNA and protein levels are suppressed by wild type VHL in two 786-0 cell transfectants. These data provide the first connection between a tumor suppressor product and TGF-β1. Given the biological actions of TGF-β1, its upregulation in cells with mutant VHL could promote tumor progression in multiple ways: by promoting angiogenesis, by enhancing stromal proliferation, by increasing collagenase, gelatinase-b activity and by suppressing the immune response to the tumor. Indeed, the concomitant dysregulation in RCCs of TGF-α, VEGF, and TGF-β1 —all VHL targets—may be particularly efficacious in this regard, since all have pro-angiogenic actions; and TGF-α, in addition, can act to directly stimulate tumor growth through an autocrine loop.

The mechanism of action of pVHL is poorly understood. It has been shown that pVHL interacts in vitro with the regulatory subunits, elongin B and C of the transcription elongation complex (elongin SIII); however, none of the target genes so far identified, including TGF-β1, appear to be regulated at the level of transcriptional elongation. Moreover, VHL interacts with Hs-Cul 2; its yeast homolog Cdc 53 is a part of ubiquitin protein ligase complex that targets cell cycle proteins for degradation by the ubiquitin proteolytic pathway (Lonerean, K. M. et al., *Mol Cell Biol* 18, 732–741 (1998) and Pause, A. et al., *Proc Natl Acad Sci USA* 94, 2156–2161 (1997)). Collectively, these data point to a role for complexes containing pVHL, elongin B, elongin C, and Cul-2 to target certain proteins, perhaps RNA binding proteins, involved in degradation of target mRNAs (Lonerean, K. M. et al., *Mol Cell Biol* 18, 732–741 (1998)).

Lack of a functional type II receptor and associated re-arrangements of the gene, or aberrations in transcription, or in post-transcriptional steps have been described in several human tumors, including gastric, colon, breast cancers, and T cell malignancies (MacKay, S. L. et al., *Ann Surg* 221, 767–776; discussion 776–767 (1995), Park, K. et al., *Proc Natl Acad Sci USA* 91, 8772–8776 (1994), Parsons, R. et al., *Cancer Res* 55, 5548–5550 (1995), Markowitz, S. et al., *Science* 268, 1336–1338 (1995), Lu, S. L., Zhang, W. C., Akiyama, Y., Nomizu, T. & Yuasa, Y., *Cancer Res* 56, 4595–4598 (1996), and Kadin, M. E. et al., *Proc Natl Acad Sci USA* 91, 6002–6006 (1994)) but not in RCC. As described herein, it is now demonstrated that 786-0 cells do not express type II receptor protein and are functionally resistant to the TGF-β signal transduction.

TGF-β1 is upregulated in several cancers. Studies to date correlating prognosis with TGF-β levels in different cancers have not all been consistent, though inverse associations have been found in hepatic, renal, cervical, and prostate cancer (Tsai, J. F. et al, *Medicine* (Baltimore) 76, 213–226 (1997), Knoefel, B. et al., *J Interferon Cytokine Res* 17, 95–102 (1997), Ivanovic, V., Melman, A., Davis-Joseph, B., Valcic, M. & Gellebter, J., *Nat Med* 1, 282–284 (1995), Friess, H. et al., *Gastroenterology* 105, 1846–1856 (1993), Junker, U. et al., *Cytokine* 8, 794–798 (1996) and Chopra, V., Dinh, T. V. & Hannigan, E N., *Cancer Invest* 16, 152–159 (1998)). Some cancer cells also secrete activated TGF-β1 (Steiner, M. S., *J Urol* 153, 1085–1096 (1995)); however RCCs secrete latent TGF-β1 predominantly (Ramp, U. et al., *J Urol* 157, 2345–2350 (1997), Ramp, U. et al., *Lab Invest* 76, 739–749 (1997), and Junker, U. et al., *Cytokine* 8, 794–798 (1996)). Moreover, cell lines derived from metastatic cancers when compared to primary cancers can show greater TGF-β1 production and resistance to its growth inhibitory effect, but increased collagenase activity (Sehgal, I., Baley, P. A. & Thompson, T. C., *Cancer Res* 56, 3359–3365 (1996)).

Multiple biological actions of TGF-β1 in the etiology of cancer can be invoked. The pro-angiogenic effects of TGFβ1 in potentiating tumor progression are likely to be important. Targeted disruption of either the TGF-β1 gene or its type II receptor results in defective placental vasculogenesis (Dickson, M. C. et al., *Development* 121, 1845–1854 (1995) and Oshima, M., Oshima, H. & Taketo, M. M., *Dev Biol* 179, 297–302 (1996)). TGF-β1 regulates other "angiogenic" molecules, such as VEGF, TGF-α, and VEGF receptor flk-1 (Massague, J. et al., *Cancer Surv* 1992,12:81–103 (1992) and Mandriota, S. J., Menoud, P. A. & Pepper, M. S., *J Biol Chem* 271, 11500–11505 (1996)) and very recently has been shown to inhibit generation of the anti-angiogenic protein, angiostatin, via modulation of the plasminogen/plasmin system (O'Mahony, C. A., Albo, D., Tuszynski, G. P. & Berger, D. H., *Surgery* 124, 388–393 (1998)).

Though TGF-β1 inhibits endothelial cell proliferation in vitro, its overall effect in vivo is pro-angiogenic (Pepper, M. S., Mandriota, S. J., Vassalli, J. D., Orci, L. & Montesano, R., *Curr Top Microbiol Immunol* 213, 31–67 (1996)). An explanation of these seemingly discrepant results is that TGF-β1 plays an important role in the resolution phase of angiogenesis by directly inhibiting endothelial cell growth and migration and reducing extracellular proteolysis. Stable transfection of TGF-β1 confers a growth advantage of Chinese hamster ovary cells in vivo but not in vitro, accompanied by an increase in capillary density; local administration of neutralizing antibody to TGF-β1 reduced both capillary density and tumor growth (Ueki, N. et al., *BiocHim Biophys Acta* 1137, 189–196 (1992)). However, a large quantity of antibody (5 mg) was used to neutralize the overexpressed TGF-β1 produced by cancer cells in contrast to 100 μg of antibody used to antagonize endogenous TGF-β1 as described herein.

Figure 4A:
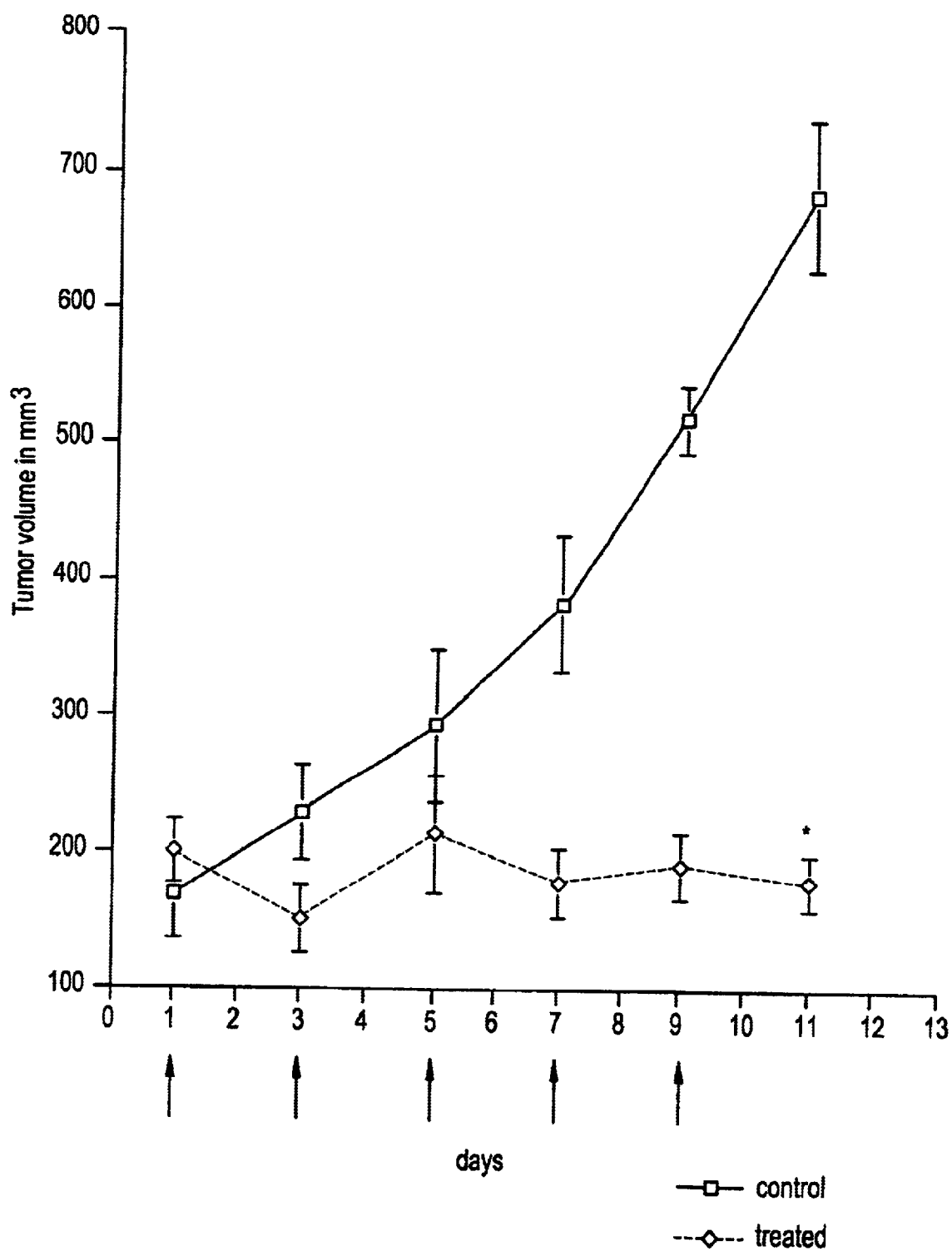
FIG. 4A is a graph showing the results of an experiment demonstrating the anti-tumor effect of neutralizing antibody against TGF-β in RCC tumors in nude beige (NK⁻)mice. When the tumor volume was approximately 150 mm$^3$, therapy was started with neutralizing antibody (100 μg) against TGF-β (treated, n=4) or control IgG (control, n=4) on alternate days (days 1–9), as indicated by arrows. The tumor size was measured on alternate days (days 1–11). Each time point represents the mean+/–SE of 4 mice in each group. The difference (*) in tumor size on day 11 between the treated and controls was statistically significant (p<0.01 using ANOVA).

TGF-β1 mediated angiogenesis is contextual, i.e., in the presence of positive regulators such as VEGF and bFGF, an additive or synergistic angiogenic response is noted. Also, the effect of TGF-β on endothelial cell function is concentration dependent, i.e., VEGF and bFGF induced capillary invasion in an in vitro 3-D model was dependent on the concentration of TGF-β1 and was the highest at 100–500 pg TGFβ1 (Pepper, M. S., Mandriota, S. J., Vassalli, J. D., Orci, L. & Montesano, R., *Curr Top Microbiol Immunol* 213, 31–67 (1996)). These facts may explain why neutralizing antibody against TGF-β did not inhibit angiogenesis in a breast cancer model (Arteaga, C. L. et al., *J Clin Invest* 92, 2569–2576 (1993)), whereas in the 786-O RCC model, VHL mutation leads to upregulation of multiple factors—VEGF, TGF-α, and TGF-β1—perhaps potentiating each other's angiogenic effects. In addition, the studies involving the breast cancer model showed no evidence of anti-angiogenic effect, and were found to inhibit cancer only in mice deficient for NK cells. The present invention, on the other hand, is equally effective in both NK$^+$ and NK$^-$ mice. The data presented in FIG. 4A is from nude beige mice, which lack NK activity, whereas FIG. 4C presents results from regular nude mice, which possess NK activity.

Despite rapid progress in characterizing cell surface receptors for TGF-β, little is known about the function of TGF-β receptors in endothelial cells, and virtually nothing is known about the role of TGF-β ligand-receptor interactions in the regulation of angiogenesis in vivo. Endothelial cells respond equally to TGFβ1 and ⊖3 and poorly, if at all, to TGF-β2, resulting perhaps from the low affinity of endoglin (type III receptor) to TGFβ2 in endothelial cells. Though the antibody used herein is panspecific (against TGF-β1, 2, and 3), the effect seen is probably mediated by neutralization of TGF-β1, because RCC cells do not express TGFβ3 and express very low levels of TGF-β2 mRNA.

TGF-β1 may also enhance carcinogenesis by suppressing the immune response (Massague, J. et al., *Cancer Surv* 1992;12:81–103 (1992), Norgaard, P., Hougaard, S., Poulsen, H. S. & Spang-Thomsen, M., *Cancer Treat Rev* 21, 367–403 (1995) and Arteaga, C. L. et al., *J Clin Invest* 92, 2569–2576 (1993)). In a nude beige mice RCC model, there are no T-cells, B cells and NK cells; hence, it is reasonable to believe that tumor suppression is predominantly from the anti-angiogenic effect, as suggested by the microvessel count data. Experiments in syngeneic RCC models might elucidate an additional therapeutic benefit of helper and cytolytic T cell activity and NK cell activity upon neutralization of TGF-β1 action. In this context, antagonizing TGF-β1 action may be particularly appropriate for the treatment of RCCs in man, since these tumors secrete numerous immunomodulatory cytokines in addition to TGF-β, including IL-10 and IL-6 (Knoefel, B. et al., *J Interferon Cytokine Res* 17, 95–102 (1997)). These cytokines diminish T cell responses to the tumor, and neutralizing part of their activity may, therefore, show unusual benefit in renal cancer therapy.

Based on the results described herein, methods are now available for inhibiting cell proliferation disease in a vertebrate. As used herein, the term "vertebrate" includes all mammals, and specifically includes humans. A "proliferative disease" includes any disease or condition affecting a vertebrate that is characterized by proliferating cells, and, preferably, cells that secrete TGF-β. Other non-proliferating cells secreting TGF-β, are also intended to be encompassed, including stromal cells, fibroblasts, macrophages, platelets, endothelial calls, granular neutrophils, and other cells. TGF-β can also induce the production of more TGF-β in surrounding cells.

The term "TGF-β" as used herein includes TGF-β1, TGFβ2 and TGF-β3. Also included are other related proteins with similar properties. The TGF-β of the invention can be secreted not only by tumor cells, but also by stromal cells, fibroblasts, macrophages, platelets, endothelial calls, granular neutrophils, and other cells. Because TGF-β can auto-regulate itself, and induce production of more TGF-β, the cells surrounding those producing TGF-β can in turn produce TGF-β. TGF-β from all of these sources is intended to be encompassed in the present invention. Also included are TGF-β antagonists. By "antagonist" is meant a molecule which inhibits the activity of TGF-β. In the present invention, a "TGF-β antagonist" can act by either binding TGF-β, binding the receptor for TGF-β, blocking the conversion of the latent form of TGF-β to the active form, blocking the secretion of TGF-β, blocking the active sites in cells that use TGF-β, preventing TGF-β from inducing production of more TGF-β in or by surrounding cells, or blocking the intracellular action of TGF-β following receptor binding.

Also encompassed by the term TGF-β are biologically active fragments, mutants, derivatives, homologs, analogs and protein or peptide mimics of TGF-β1, TGFβ2 and TGF-β3. A "fragment" of TGF-β is any amino acid sequence shorter that the TGF-β molecule, comprising at least 25 consecutive amino acids of the TGF-β polypeptide. Such molecules may or may not also comprise additional amino acids derived from the process of cloning, e.g., amino acid residues or amino acid sequences corresponding to full or partial linker sequences. To be encompassed by the present invention, such mutants, with or without such additional amino acid residues, must have substantially the same biological activity as the natural or full-length version of the reference polypeptide.

By "mutant" of TGF-β is meant a polypeptide that includes any change in the amino acid sequence relative to the amino acid sequence of the equivalent reference TGF-β polypeptide. Such changes can arise either spontaneously or by manipulations by man, by chemical energy (e.g., X-ray), or by other forms of chemical mutagenesis, or by genetic engineering, or as a result of mating or other forms of exchange of genetic information. Mutations include, e.g., base changes, deletions, insertions, inversions, translocations, or duplications. Mutant forms of TGF-β may display either increased or decreased anti-angiogenic activity relative to the equivalent reference TGF-β polynucleotide, and such mutants may or may not also comprise additional amino acids derived from the process of cloning, e.g., amino acid residues or amino acid sequences corresponding to full or partial linker sequences.

Mutants/fragments of the anti-angiogenic proteins of the present invention can be generated by PCR cloning. To make such fragments, PCR primers are designed from known sequence in such a way that each set of primers will amplify known subsequence from the overall protein. These subsequences are then cloned into an appropriate expression vector, such as the pET22b vector, and the expressed protein tested for its anti-angiogenic activity as described in the assays below. Mutants/fragments of the anti-angiogenic proteins of the present invention can also be generated by *Pseudomonas elastase* digestion, as described by Mariyama, M. et al. (1992, *J Biol Chem* 267,1253–8).

By "analog" of TGF-β is meant a non-natural molecule substantially similar to either the entire TGF-β molecule or a fragment or allelic variant thereof, and having substantially the same or superior biological activity. Such analogs are intended to include derivatives (e.g., chemical derivatives, as defined above) of the biologically active TGF-β, as well as its fragments, mutants, homologs, and allelic variants, which derivatives exhibit a qualitatively similar agonist or antagonist effect to that of the unmodified TGF-β polypeptide, fragment, mutant, homolog, or allelic variant.

By "allele" of TGF-β is meant a polypeptide sequence containing a naturally-occurring sequence variation relative to the polypeptide sequence of the reference TGF-β polypeptide. By "allele" of a polynucleotide encoding the TGF-β polypeptide is meant a polynucleotide containing a sequence variation relative to the reference polynucleotide sequence encoding the reference TGF-β polypeptide, where the allele of the polynucleotide encoding the TGF-β polypeptide encodes an allelic form of the TGF-β polypeptide.

It is possible that a given polypeptide may be either a fragment, a mutant, an analog, or allelic variant of TGF-β, or it may be two or more of those things, e.g., a polypeptide may be both an analog and a mutant of the TGF-β polypeptide. For example, a shortened version of the TGF-β molecule (e.g., a fragment of TGF-β) may be created in the laboratory. If that fragment is then mutated through means known in the art, a molecule is created that is both a fragment and a mutant of TGF-β. In another example, a mutant may be created, which is later discovered to exist as an allelic form of TGF-β in some mammalian individuals. Such a mutant TGF-β molecule would therefore be both a mutant and an allelic variant. Such combinations of fragments, mutants, allelic variants, and analogs are intended to be encompassed in the present invention.

Encompassed by the present invention are proteins that have substantially the same amino acid sequence as TGF-β, or polynucleotides that have substantially the same nucleic acid sequence as the polynucleotides encoding TGF-β. "Substantially the same sequence" means a nucleic acid or polypeptide that exhibits at least about 70% sequence identity with a reference sequence, e.g., another nucleic acid or polypeptide, typically at least about 80% sequence identity with the reference sequence, preferably at least about 90% sequence identity, more preferably at least about 95% identity, and most preferably at least about 97% sequence identity with the reference sequence. The length of comparison for sequences will generally be at least 75 nucleotide bases or 25 amino acids, more preferably at least 150 nucleotide bases or 50 amino acids, and most preferably 243–264 nucleotide bases or 81–88 amino acids. "Polypeptide" as used herein indicates a molecular chain of amino acids and does not refer to a specific length of the product. Thus, peptides, oligopeptides and proteins are included within the definition of polypeptide. This term is also intended to include polypeptide that have been subjected to post-expression modifications such as, for example, glycosylations, acetylations, phosphorylations and the like.

"Sequence identity," as used herein, refers to the subunit sequence similarity between two polymeric molecules, e.g., two polynucleotides or two polypeptides. When a subunit position in both of the two molecules is occupied by the same monomeric subunit, e.g., if a position in each of two peptides is occupied by serine, then they are identical at that position. The identity between two sequences is a direct function of the number of matching or identical positions, e.g., if half (e.g., 5 positions in a polymer 10 subunits in length), of the positions in two peptide or compound sequences are identical, then the two sequences are 50% identical; if 90% of the positions, e.g., 9 of 10 are matched, the two sequences share 90% sequence identity. By way of example, the amino acid sequences $R_2R_5R_7R_{10}R_6R_3$ and $R_9R_8R_1R_{10}R_6R_3$ have 3 of 6 positions in common, and therefore share 50% sequence identity, while the sequences $R_2R_5R_7R_{10}R_6R_3$ and $R_8R_1R_{10}R_6R_3$ have 3 of 5 positions in common, and therefore share 60% sequence identity. The identity between two sequences is a direct function of the number of matching or identical positions. Thus, if a portion of the reference sequence is deleted in a particular peptide, that deleted section is not counted for purposes of calculating sequence identity, e.g., $R_2R_5R_7R_{10}R_6R_3$ and $R_2R_5R_7R_{10}R_3$ have 5 out of 6 position in common, and therefore share 83.3% sequence identity.

Identity is often measured using sequence analysis software e.g., BLASTN or BLASTP. The default parameters for comparing two sequences (e.g., "Blast"-ing two sequences against each other, by BLASTN (for nucleotide sequences) are reward for match=1, penalty for mismatch=-2, open gap=5, extension gap=2. When using BLASTP for protein sequences, the default parameters are reward for match=0, penalty for mismatch=0, open gap=11, and extension gap=1.

When two sequences share "sequence homology," it is meant that the two sequences differ from each other only by conservative substitutions. For polypeptide sequences, such conservative substitutions consist of substitution of one amino acid at a given position in the sequence for another amino acid of the same class (e.g., amino acids that share characteristics of hydrophobicity, charge, pK or other conformational or chemical properties, e.g., valine for leucine, arginine for lysine), or by one or more nonconservative amino acid substitutions, deletions, or insertions, located at positions of the sequence that do not alter the conformation or folding of the polypeptide to the extent that the biological activity of the polypeptide is destroyed. Examples of "conservative substitutions" include substitution of one nonpolar (hydrophobic) residue such as isoleucine, valine, leucine or methionine for another; the substitution of one polar (hydrophilic) residue for another such as between arginine and lysine, between glutamine and asparagine, between threonine and serine; the substitution of one basic residue such as lysine, arginine or histidine for another; or the substitution of one acidic residue, such as aspartic acid or glutamic acid for another; or the use of a chemically derivatized residue in place of a non-derivatized residue; provided that the polypeptide displays the requisite biological activity. Two sequences which share sequence homology may called "sequence homologs."

Homology, for polypeptides, is typically measured using sequence analysis software (e.g., Sequence Analysis Software Package of the Genetics Computer Group, University of Wisconsin Biotechnology Center, 1710 University Avenue, Madison, Wis. 53705). Protein analysis software matches similar sequences by assigning degrees of homology to various substitutions, deletions, and other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine.

Also encompassed by the present invention are chemical derivatives of TGF-β. "Chemical derivative" refers to a subject polypeptide having one or more residues chemically derivatized by reaction of a functional side group. Such derivatized residues include for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups may be derivatized to form salts, methyl and ethyl esters or other types of esters or hydrazides. Free hydroxyl groups may be derivatized to form O-acyl or O-alkyl derivatives. The imidazole nitrogen of histidine may be derivatized to form N-imbenzylhistidine. Also included as chemical derivatives are those peptides which contain one or more naturally occurring amino acid derivatives of the twenty standard amino acids. For examples: 4-hydroxyproline may be substituted for proline; 5-hydroxylysine may be substitute for lysine; 3-methylhistidine may be substituted for histidine; homoserine may be substituted for serine; and ornithine may be substituted for lysine.

The present invention also includes fusion proteins and chimeric proteins comprising the anti-angiogenic proteins, their fragments, mutants, homologs, analogs, and allelic variants. A fusion or chimeric protein can be produced as a result of recombinant expression and the cloning process, e.g., the protein may be produced comprising additional amino acids or amino acid sequences corresponding to full or partial linker sequences, e.g., a histidine tag. As used herein, the term "fusion or chimeric protein" is intended to encompass changes of this type to the original protein sequence. A fusion or chimeric protein can consist of a multimer of a single protein, e.g., repeats of the antiangiogenic proteins, or the fusion and chimeric proteins can be made up of several proteins, e.g., several of the anti-angiogenic proteins. The fusion or chimeric protein can comprise a combination of two or more known anti-angiogenic proteins (e.g., angiostatin and endostatin, or biologically active fragments of angiostatin and endostatin), or an anti-angiogenic protein in combination with a targeting agent (e.g., endostatin with epidermal growth factor (EGF) or RGD peptides), or an anti-angiogenic protein in combination with an immunoglobulin molecule (e.g., endostatin and IgG, specifically with the Fc portion removed). The fusion and chimeric proteins can also include the anti-angiogenic proteins, their fragments, mutants, homologs, analogs, and allelic variants, and other anti-angiogenic proteins, e.g., endostatin, or angiostatin. Other anti-angiogenic proteins can include restin and apomigren; (WO 99/29856, the teachings of which are herein incorporated by reference) and fragments of endostatin (WO 99/29855, the teachings of which are herein incorporated by reference). The term "fusion protein" or "chimeric protein" as used herein can also encompass additional components for e.g., delivering a chemotherapeutic agent, wherein a polynucleotide encoding the chemotherapeutic agent is linked to the polynucleotide encoding the anti-angiogenic protein. Fusion or chimeric proteins can also encompass multimers of an anti-angiogenic protein, e.g., a dimer or trimer. Such fusion or chimeric proteins can be linked together via post-translational modification (e.g., chemically linked), or the entire fusion protein may be made recombinantly.

Multimeric proteins comprising TGF-β, its fragments, mutants, homologs, analogs and allelic variants are also intended to be encompassed by the present invention. By "multimer" is meant a protein comprising two or more copies of a subunit protein. The subunit protein may be one of the proteins of the present invention, e.g., TGF-β repeated two or more times, or a fragment, mutant, homolog, analog or allelic variant, e.g., a TGF-β mutant or fragment repeated two or more times. Such a multimer may also be a fusion or chimeric protein, e.g., a repeated TGF-β mutant may be combined with polylinker sequence, and/or one or more anti-angiogenic peptides, which may be present in a single copy, or may also be tandemly repeated, e.g. a protein may comprise two or more multimers within the overall protein.

Proteins related to those of the present invention can also be isolated by using probes designed from the proteins of the present invention. Exceptional methods are provided in U.S. Pat. No. 5,837,490, by Jacobs et al., the entire teachings of which are herein incorporated by reference in their entirety. The design of the oligonucleotide probe should preferably follow these parameters: (a) It should be designed to an area of the sequence which has the fewest ambiguous bases ("N's"), if any, and (b) it should be designed to have a $T_m$ of approx. 80° C. (assuming 2° C. for each A or T and 4 degrees for each G or C).

The oligonucleotide should preferably be labeled with g-$^{32}$P-ATP (specific activity 6000 Ci/mmole) and T4 polynucleotide kinase using commonly employed techniques for labeling 2 oligonucleotides. Other labeling techniques can also be used. Unincorporated label should preferably be removed by gel filtration chromatography or other established methods. The amount of radioactivity incorporated into the probe should be quantitated by measurement in a scintillation counter. Preferably, specific activity of the resulting probe should be approximately $4\times10^6$ dpm/pmole. The bacterial culture containing the pool of full-length clones should preferably be thawed and 100 μl of the stock used to inoculate a sterile culture flask containing 25 ml of sterile L-broth containing ampicillin at 100 μg/ml. The culture should preferably be grown to saturation at 37° C., and the saturated culture should preferably be diluted in fresh L-broth. Aliquots of these dilutions should preferably be plated to determine the dilution and volume which will yield approximately 5000 distinct and well-separated colonies on solid bacteriological media containing L-broth containing ampicillin at 100 μg/ml and agar at 1.5% in a 150 mm petri dish when grown overnight at 37° C. Other known methods of obtaining distinct, well-separated colonies can also be employed.

Standard colony hybridization procedures should then be used to transfer the colonies to nitrocellulose filters and lyse, denature and bake them. Highly stringent condition are those that are at least as stringent as, for example, 1×SSC at 65° C., or 1×SSC and 50% formamide at 42° C. Moderate stringency conditions are those that are at least as stringent as 4×SSC at 65° C., or 4×SSC and 50% formamide at 42° C. Reduced stringency conditions are those that are at least as stringent as 4×SSC at 50° C., or 6×SSC and 50% formamide at 40° C.

The filter is then preferably incubated at 65° C. for 1 hour with gentle agitation in 6×SSC (20× stock is 175.3 g NaCl/liter, 88.2 g Na citrate/liter, adjusted to pH 7.0 with NaOH) containing 0.5% SDS, 100 μg/ml of yeast RNA, and 10 mM EDTA (approximately 10 mL per 150 mm filter). Preferably, the probe is then added to the hybridization mix at a concentration greater than or equal to $1\times10^6$ dpm/mL. The filter is then preferably incubated at 65° C. with gentle agitation overnight. The filter is then preferably washed in 500 mL of 2×SSC/0.5% SDS at room temperature without agitation, preferably followed by 500 mL of 2×SSC/0.1% SDS at room temperature with gentle shaking for 15 minutes. A third wash with 0.1×SSC/0.5% SDS at 65° C. for 30 minutes to 1 hour is optional. The filter is then preferably dried and subjected to autoradiography for sufficient time to visualize the positives on the X-ray film. Other known hybridization methods can also be employed. The positive colonies are then picked, grown in culture, and plasmid DNA isolated using standard procedures. The clones can then be verified by restriction analysis, hybridization analysis, or DNA sequencing.

Polynucleotides encoding TGF-β can be cloned out of isolated DNA or a cDNA library. Nucleic acids polypeptides, referred to herein as "isolated" are nucleic acids or polypeptides substantially free (i.e., separated away from) the material of the biological source from which they were obtained (e.g., as exists in a mixture of nucleic acids or in cells), which may have undergone further processing. "Isolated" nucleic acids or polypeptides include nucleic acids or polypeptides obtained by methods described herein, similar methods, or other suitable methods, including essentially pure nucleic acids or polypeptides, nucleic acids or polypeptides produced by chemical synthesis, by combinations of chemical or biological methods, and recombinantly produced nucleic acids or polypeptides which are isolated. An isolated polypeptide therefore means one which is relatively free of other proteins, carbohydrates, lipids, and other cellular components with which it is normally associated. An isolated nucleic acid is not immediately contiguous with (i.e., covalently linked to) both of the nucleic acids with which it is immediately contiguous in the naturally-occurring genome of the organism from which the nucleic acid is derived. The term, therefore, includes, for example, a nucleic acid which is incorporated into a vector (e.g., an autonomously replicating virus or plasmid), or a nucleic acid which exists as a separate molecule independent of other nucleic acids such as a nucleic acid fragment produced by chemical means or restriction endonuclease treatment.

Proliferative diseases encompassed by the present invention are further characterized by angiogenesis, or angiogenic activity. As used herein, the term "angiogenesis" means the generation of new blood vessels into a tissue or organ, and involves endothelial cell proliferation. Under normal physiological conditions, humans or animals undergo angiogenesis only in very specific restricted situations. For example, angiogenesis is normally observed in wound healing, fetal and embryonal development, and formation of the corpus luteum, endometrium and placenta. The term "endothelium" means a thin layer of flat epithelial cells that lines serous cavities, lymph vessels, and blood vessels. "Anti-angiogenic activity" therefore refers to the capability of a composition to inhibit the growth of blood vessels. The growth of blood vessels is a complex series of events, and includes localized breakdown of the basement membrane lying under the individual endothelial cells, proliferation of those cells, migration of the cells to the location of the future blood vessel, reorganization of the cells to form a new vessel membrane, cessation of endothelial cell proliferation, and, incorporation of pericytes and other cells that support the new blood vessel wall. "Anti-angiogenic activity" as used herein therefore includes interruption of any or all of these stages, with the end result that formation of new blood vessels is inhibited.

Anti-angiogenic activity may include endothelial inhibiting activity, which refers to the capability of a composition to inhibit angiogenesis in general and, for example, to inhibit the growth or migration of bovine capillary endothelial cells in culture in the presence of fibroblast growth factor, angiogenesis-associated factors, or other known growth factors. A "growth factor" is a composition that stimulates the growth, reproduction, or synthetic activity of cells. An "angiogenesis-associated factor" is a factor which either inhibits or promotes angiogenesis. An example of an angiogenesis-associated factor is an angiogenic growth factor, such as basic fibroblastic growth factor (bFGF), which is an angiogenesis promoter. Another example of an angiogenesis-associated factor is an angiogenesis inhibiting factor such as e.g., those described in U.S. Pat. Nos. 5,567, 609, 5,691,182, and 5,856,184, angiostatin (see, e.g., U.S. Pat. Nos. 5,801,012, 5,837,682, 5,733,876, 5,776,704, 5,639,725, 5,792,845, WO 96/35774, WO 95/29242, WO 96/41194, WO 97/23500), endostatin (see, e.g., WO 97/15666), Restin (WO 99/29856, "Restin and Methods of Use Thereof" by Vikas P. Sukhatme, filed Dec. 8, 1998, and its U.S. designation, Ser. No. 09/589,774), EM1 (WO 99/29855, "Mutants of Endostatin, 'EM 1' Having Anti-Angiogenic Activity and Methods of Use Thereof," by Vikas P. Sukhatme, filed Dec. 8, 1998, and its U.S. designation, Ser. No. 09/589,777), Arresten, Canstatin, and Tumstatin (PCT/US99/13737, "Anti-Angiogenic Proteins and Methods of Use Thereof," by Raghuram Kalluri, filed Jun. 17, 1999), or fragments or mutants thereof. The teachings of all of these patents and patent applications are herein incorporated by reference in their entirety.

By "substantially the same biological activity" or "substantially the same or superior biological activity" is meant that a composition has anti-angiogenic activity, and behaves similarly as do other anti-angiogenic compounds, as determined in standard assays. "Standard assays" include, but are not limited to, those protocols used in the molecular biological arts to assess anti-angiogenic activity, cell cycle arrest, and apoptosis. Such assays include, but are not limited to, assays of endothelial cell proliferation, endothe-lial cell migration, cell cycle analysis, and endothelial cell tube formation, detection of apoptosis, e.g., by apoptotic cell morphology or Annexin V-FITC assay, chorioallantoic membrane (CAM) assay, and inhibition of renal cancer tumor growth in nude mice. Such assays are provided in patent applications WO 99/29856, "Restin and Methods of Use Thereof," by Vikas P. Sukhatme, filed Dec. 8, 1998, and its U.S. designation, Ser. No. 09/589,777, WO 99/29855, "Mutants of Endostatin, 'EM 1' Having Anti-Angiogenic Activity and Methods of Use Thereof," by Vikas P. Sukhatme, filed Dec. 8, 1998, and its U.S. designation, Ser. No. 09/589,777, and WO 99/29878, "Methods of Producing Anti-Angiogenic Proteins," by Vikas P. Sukhatme, filed Dec. 8, 1998, and its U.S. designation, Ser. No. 09/589,483, the teachings of all of which are herein incorporated by reference in their entirety.

Such diseases include benign tumors, malignant tumors, rheumatoid arthritis, psoriasis, ocular angiogenesis diseases, Osler-Webber Syndrome, myocardial angiogenesis, plaque neovascularization, graft and post-angioplasty stenosis, telaniectasia, hemophiliac joints, angiofibroma, wound granulation, intestinal adhesions, atherosclerosis, scleroderma, hypertrophic scars, cat scratch disease, and *Heliobacter pylori* ulcers.

In particular, the inhibition of TGF-$\beta$-mediated angiogenesis results in the inhibition of tumor growth. Tumor growth can be determined using techniques described herein, and other techniques well-known to those of skill in the art. In addition, inhibition of TGF-$\beta$-mediated angiogenesis can result in regression of established tumors. Tumor regression can be determined as described herein, and by other techniques well-known to those of skill in the art.

The inhibition of TGF-$\beta$-mediated angiogenisis can be accomplished in a number of ways. For example, the proliferating cells (e.g., tumor cells) can be contacted with molecules that inhibit TGF-$\beta$-mediated angiogenic activity. For example, an antibody that inhibits or neutralizes TGF-$\beta$ activity can be used to render the TGF-$\beta$ ineffective. Appropriate antibodies, including monoclonal antibodies, are described in U.S. Pat. No. 5,571,714 and British Patent Application GB 2 305 921 A, which are herein incorporated by reference in their entirety. Antibodies encompassed by the present invention will specifically bind to TGF-$\beta$, or a fragment thereof. Methods of determining specific binding activity of antibodies to their ligand/antigens are well-known to those of skill in the art.

The invention encompasses antibodies and antisera, which can be used for testing of novel TGF-$\beta$, and can also be used in diagnosis, prognosis, or treatment of diseases and conditions characterized by, or associated with, angiogenic activity or lack thereof. Such antibodies and antisera can also be used to up-regulate angiogenesis where desired, e.g., in post-infarct heart tissue, antibodies or antisera to the proteins of the invention can be used to block localized, native anti-angiogenic proteins and processes, and increase formation of new blood vessels and inhibit atrophy of heart tissue.

Such antibodies and antisera can be combined with pharmaceutically-acceptable compositions and carriers to form diagnostic, prognostic or therapeutic compositions. The term "antibody" or "antibody molecule" refers to a population of immunoglobulin molecules and/or immunologically active portions of immunoglobulin molecules, i.e., molecules that contain an antibody combining site or paratope.

Passive antibody therapy using antibodies that specifically bind the TGF-$\beta$ can be employed to modulate angiogenic-dependent processes such as reproduction, development, and wound healing and tissue repair. In addition, antisera directed to the Fab regions of antibodies of the TGF-β can be administered to block the ability of endogenous antisera to the proteins to bind the proteins.

The TGF-β of the present invention also can be used to generate antibodies that are specific for the inhibitor(s) and receptor(s). TGF-β receptors are known, and have been isolated (Goggins, M. et al., *Cancer Res* 58, 5329–5332 (1998)). The antibodies can be either polyclonal antibodies or monoclonal antibodies. These antibodies that specifically bind to the TGF-β or their receptors can be used in diagnostic methods and kits that are well known to those of ordinary skill in the art to detect or quantify the TGF-β or its receptors in a body fluid or tissue. Results from these tests can be used to diagnose or predict the occurrence or recurrence of a cancer and other angiogenic mediated diseases.

The invention also includes use of the TGF-β, antibodies thereto, and compositions comprising those proteins and/or their antibodies in diagnosis or prognosis of diseases characterized by angiogenic activity. As used herein, the term "prognostic method" means a method that enables a prediction regarding the progression of a disease of a human or animal diagnosed with the disease, in particular, an angiogenesis dependent disease. The term "diagnostic method" as used herein means a method that enables a determination of the presence or type of angiogenesis-dependent disease in or on a human or animal.

The TGF-β can be used in a diagnostic method and kit to detect and quantify antibodies capable of binding the proteins. These kits would permit detection of circulating antibodies to the TGF-β which indicates the spread of micrometastases in the presence of the TGF-β secreted by primary tumors in situ. Patients that have such circulating anti-protein antibodies may be more likely to develop multiple tumors and cancers, and may be more likely to have recurrences of cancer after treatments or periods of remission. The Fab fragments of these anti-protein antibodies may be used as antigens to generate anti-protein Fab-fragment antisera which can be used to neutralize anti-protein antibodies. Such a method would reduce the removal of circulating protein by anti-protein antibodies, thereby effectively elevating circulating levels of the TGF-β.

The present invention also includes isolation of receptors specific for the TGF-β. Protein fragments that possess high affinity binding to tissues can be used to isolate the receptor of the TGF-β on affinity columns. Isolation and purification of the receptor(s) is a fundamental step towards elucidating the mechanism of action of the TGF-β. Isolation of a receptor and identification of agonists and antagonists will facilitate development of drugs to modulate the activity of the receptor, the final pathway to biological activity. Isolation of the receptor enables the construction of nucleotide probes to monitor the location and synthesis of the receptor, using in situ and solution hybridization technology. Further, the gene for the receptor can be isolated, incorporated into an expression vector and transfected into cells, such as patient tumor cells to increase the ability of a cell type, tissue or tumor to bind the TGF-β and inhibit local angiogenesis.

The TGF-β is employed to develop affinity columns for isolation of the receptor(s) for the TGF-β from cultured tumor cells. Isolation and purification of the receptor is followed by amino acid sequencing. Using this information the gene or genes coding for the receptor can be identified and isolated. Next, cloned nucleic acid sequences are developed for insertion into vectors capable of expressing the receptor. These techniques are well known to those skilled in the art. Transfection of the nucleic acid sequence(s) coding for the receptor into tumor cells, and expression of the receptor by the transfected tumor cells enhances the responsiveness of these cells to endogenous or exogenous TGF-β and thereby decreasing the rate of metastatic growth.

TGF-β of the present invention can be synthesized in a standard microchemical facility and purity checked with HPLC and mass spectrophotometry. Methods of protein synthesis, HPLC purification and mass spectrophotometry are commonly known to those skilled in these arts. The TGF-β and its receptor proteins are also produced in recombinant *E. coli* or yeast expression systems, and purified with column chromatography.

Different protein fragments of the intact TGF-β can be synthesized for use in several applications including, but not limited to the following; as antigens for the development of specific antisera, as agonists and antagonists active at binding sites of the TGF-β, as proteins to be linked to, or used in combination with, cytotoxic agents for targeted killing of cells that bind the TGF-β.

The synthetic protein fragments of the TGF-β have a variety of uses. The protein that binds to the receptor(s) of the TGF-β with high specificity and avidity is radiolabeled and employed for visualization and quantitation of binding sites using autoradiographic and membrane binding techniques. This application provides important diagnostic and research tools. Knowledge of the binding properties of the receptor(s) facilitates investigation of the transduction mechanisms linked to the receptor(s).

The TGF-β and proteins derived from it can be coupled to other molecules using standard methods. Tyrosine and lysine residues at the amino and carboxyl termini of the TGF-β can be isotopically and nonisotopically labeled with many techniques, for example radiolabeling using conventional techniques (tyrosine residues-chloramine T, iodogen, lactoperoxidase; lysine residues-Bolton-Hunter reagent). These coupling techniques are well known to those skilled in the art. Alternatively, tyrosine or lysine is added to fragments that do not have these residues to facilitate labeling of reactive amino and hydroxyl groups on the protein. The coupling technique is chosen on the basis of the functional groups available on the amino acids including, but not limited to amino, sulfhydral, carboxyl, amide, phenol, and imidazole. Various reagents used to effect these couplings include among others, glutaraldehyde, diazotized benzidine, carbodiimide, and p-benzoquinone.

The TGF-β is chemically coupled to isotopes, enzymes, carrier proteins, cytotoxic agents, fluorescent molecules, chemiluminescent, bioluminescent and other compounds for a variety of applications. The efficiency of the coupling reaction is determined using different techniques appropriate for the specific reaction. For example, radiolabeling of a TGF-β of the present invention with $^{125}I$ is accomplished using chloramine T and $Na^{125}I$ of high specific activity. The reaction is terminated with sodium metabisulfite and the mixture is desalted on disposable columns. The labeled protein is eluted from the column and fractions are collected. Aliquots are removed from each fraction and radioactivity measured in a gamma counter. In this manner, the unreacted $Na^{125}I$ is separated from the labeled protein. The protein fractions with the highest specific radioactivity are stored for subsequent use such as analysis of the ability to bind to antisera of the TGF-β.

In addition, labeling the TGF-β with short lived isotopes enables visualization of receptor binding sites in vivo using positron emission tomography or other modern radiographic techniques to locate tumors with the proteins' binding sites.

Systematic substitution of amino acids within these synthesized proteins yields high affinity protein agonists and antagonists to the receptor(s) of the TGF-β that enhances or diminishes binding to the receptor(s). Such agonists are used to suppress the growth of micrometastases, thereby limiting the spread of cancer. Antagonists to the TGF-β are applied in situations of inadequate vascularization, to block the inhibitory effects of the TGF-β and promote angiogenesis. For example, this treatment may have therapeutic effects to promote wound healing in diabetics.

Other molecules that bind to TGF-β and inhibit or neutralize TGF-β activity are also encompassed by the present invention. For example, decorin is a leucine-rich proteoglycan with ubiquitous tissue distribution that has been associated with cell proliferation (Santra, M. et al. *Proc Natl Acad Sci USA* 92, 7016–7020, 1995). Also, molecules that bind the TGF-β receptors, or prevent the conversion of the latent to the active form of TGF-β, or antisense molecules that prevent TGF-β secretion, or inactivate the intracellular sites within cells that bind TGF-β, or prevent the autoregulation (induction) of TGF-β, are also encompassed by the present invention.

Another TGF-β inhibiting molecule encompassed by the present invention is latency-associated peptide (LAP), which is a molecule that binds TGF-β, and serves as a TGF-β antagonist (see, e.g., Yang, Y. et al., *Biochem* 36, 11923–11932, 1997).

Soluble forms of the TGF-β receptors, for example the TGF-βI, II, and III receptors are also encompassed by the methods of the present invention. Such receptors are described by Goggins, M. et al. (*Cancer Res* 58, 5329–5332 (1998)).

TGF-β antagonists can also be used to inhibit TGF-β activity. Such antagonists are described by Huang, S. S. et al. (*J Biol Chem* 272, 27155–27159 (1997)), and include several synthetic pentacosapeptides whose amino acids correspond to amino acid residues in TGF-β1, TGF-β2, and TGF-β3.

Specifically, the TGF-β inhibitor molecules of the present invention are contacted with the cells that are secreting TGF-β, or are deposited in the proximity of the cells that are secreting the TGF-β, in a manner such that the activity of the TGF-β protein is inhibited or neutralized. Such delivery techniques are well-known to those of skill in the art. For example, the present invention includes methods of treating an angiogenesis-mediated disease with an effective amount of a TGF-β antagonist, or antibodies to TGF-β, or one or more biologically active fragments thereof, or combinations of fragments that possess anti-angiogenic activity, or agonists and antagonists. An effective amount of the TGF-β antagonist is an amount sufficient to inhibit the angiogenesis which results in the disease or condition, thus completely, or partially, alleviating the disease or condition. Alleviation of the angiogenesis-mediated disease can be determined by observing an alleviation of symptoms of the disease, e.g., a reduction in the size of a tumor, or arrested tumor growth. As used herein, the term "effective amount" also means the total amount of each active component of the composition or method that is sufficient to show a meaningful patient benefit, i.e., treatment, healing, prevention or amelioration of the relevant medical condition, or an increase in rate of treatment, healing, prevention or amelioration of such conditions. When applied to a combination, the term refers to combined amounts of the active ingredients that result in the therapeutic effect, whether administered in combination, serially or simultaneously. Angiogenesis-mediated diseases include, but are not limited to, cancers, solid tumors, blood-born tumors (e.g., leukemias), tumor metastasis, benign tumors (e.g., hemangiomas, acoustic neuromas, neurofibromas, trachomas, and pyogenic granulomas), rheumatoid arthritis, psoriasis, ocular angiogenic diseases (e.g., diabetic retinopathy, retinopathy of prematurity, macular degeneration, corneal graft rejection, neovascular glaucoma, retrolental fibroplasia, rubeosis), Osler-Webber Syndrome, myocardial angiogenesis, plaque neovascularization, telangiectasia, hemophiliac joints, angiofibroma, and wound granulation. The TGF-β antagonist is useful in the treatment of diseases of excessive or abnormal stimulation of endothelial cells. These diseases include, but are not limited to, intestinal adhesions, Crohn's disease, atherosclerosis, scleroderma, and hypertrophic scars (i.e., keloids). The TGF-β antagonist can be used as a birth control agent by preventing vascularization required for embryo implantation. TGF-β antagonists are useful in the treatment of diseases that have angiogenesis as a pathologic consequence such as cat scratch disease (*Rochele minalia quintosa*) and ulcers (*Heliobacter pylori*). The antagonists can also be used to prevent dialysis graft vascular access stenosis, and obesity, e.g., by inhibiting capillary formation in adipose tissue, thereby preventing its expansion. TGF-β antagonists can also be used to treat localized (e.g., nonmetastisized) diseases. "Cancer" means neoplastic growth, hyperplastic or proliferative growth or a pathological state of abnormal cellular development and includes solid tumors, non-solid tumors, and any abnormal cellular proliferation, such as that seen in leukemia. As used herein, "cancer" also means angiogenesis-dependent cancers and tumors, i.e., tumors that require for their growth (expansion in volume and/or mass) an increase in the number and density of the blood vessels supplying them with blood. "Regression" refers to the reduction of tumor mass and size as determined using methods well-known to those of skill in the art.

Alternatively, where an increase in angiogenesis is desired, e.g., in wound healing, or in post-infarct heart tissue, antibodies or antisera to the TGF-β proteins can be used to block localized, native anti-angiogenic proteins and processes, and thereby increase formation of new blood vessels so as to inhibit atrophy of tissue.

The TGF-β antagonists may be used in combination with other compositions and procedures for the treatment of diseases. For example, a tumor may be treated conventionally with surgery, radiation, chemotherapy, or immunotherapy, combined with the TGF-β antagonists and then the TGF-β antagonists may be subsequently administered to the patient to extend the dormancy of micrometastases and to stabilize and inhibit the growth of any residual primary tumor. The TGF-β antagonists, or antagonistic TGF-β fragments, antisera, receptor agonists, or receptor antagonists thereof, or combinations thereof, can also be combined with other anti-angiogenic compounds, or proteins, fragments, antisera, receptor agonists, receptor antagonists of other anti-angiogenic proteins (e.g., angiostatin, endostatin). Additionally, the TGF-β antagonists, or antagonistic TGF-β fragments, antisera, receptor agonists, receptor antagonists, or combinations thereof, are combined with pharmaceutically acceptable excipients, and optionally sustained-release matrix, such as biodegradable polymers, to form therapeutic compositions. The compositions of the present invention may also contain other anti-angiogenic proteins or chemical compounds, such as endostatin or angiostatin, and mutants, fragments, and analogs thereof. The compositions may further contain other agents which either enhance the activity of the antagonist or compliment its activity or use in treatment, such as chemotherapeutic or radioactive agents. Such additional factors and/or agents may be included in the composition to produce a synergistic effect with TGF-β antagonists of the invention, or to minimize side effects. Additionally, administration of the composition of the present invention may be administered concurrently with other therapies, e.g., administered in conjunction with a chemotherapy or radiation therapy regimen.

The invention includes methods for inhibiting angiogenesis in mammalian tissues by contacting the tissue with a composition comprising the TGF-β antagonists of the invention. By "contacting" is meant not only topical application, but also those modes of delivery that introduce the composition into the tissues, or into the cells of the tissues.

Use of timed release or sustained release delivery systems are also included in the invention. Such systems are highly desirable in situations where surgery is difficult or impossible, e.g., patients debilitated by age or the disease course itself, or where the risk-benefit analysis dictates control over cure.

A sustained-release matrix, as used herein, is a matrix made of materials, usually polymers, which are degradable by enzymatic or acid/base hydrolysis or by dissolution. Once inserted into the body, the matrix is acted upon by enzymes and body fluids. The sustained-release matrix desirably is chosen from biocompatible materials such as liposomes, polylactides (polylactic acid), polyglycolide (polymer of glycolic acid), polylactide co-glycolide (co-polymers of lactic acid and glycolic acid) polyanhydrides, poly(ortho)esters, polyproteins, hyaluronic acid, collagen, chondroitin sulfate, carboxylic acids, fatty acids, phospholipids, polysaccharides, nucleic acids, polyamino acids, amino acids such as phenylalanine, tyrosine, isoleucine, polynucleotides, polyvinyl propylene, polyvinylpyrrolidone and silicone. A preferred biodegradable matrix is a matrix of one of either polylactide, polyglycolide, or polylactide co-glycolide (co-polymers of lactic acid and glycolic acid).

The angiogenesis-modulating composition of the present invention may be a solid, liquid or aerosol and may be administered by any known route of administration. Examples of solid compositions include pills, creams, and implantable dosage units. The pills may be administered orally, the therapeutic creams may be administered topically. The implantable dosage unit may be administered locally, for example at a tumor site, or which may be implanted for systemic release of the angiogenesis-modulating composition, for example subcutaneously. Examples of liquid composition include formulations adapted for injection subcutaneously, intravenously, intraarterially, and formulations for topical and intraocular administration. Examples of aerosol formulation include inhaler formulation for administration to the lungs.

The TGF-β antagonists with the activity described above can be provided as isolated and substantially purified proteins and protein fragments in pharmaceutically acceptable formulations using formulation methods known to those of ordinary skill in the art. These formulations can be administered by standard routes. In general, the combinations may be administered by the topical, transdermal, intraperitoneal, intracranial, intracerebroventricular, intracerebral, intravaginal, intrauterine, oral, rectal or parenteral (e.g., intravenous, intraspinal, subcutaneous or intramuscular) route. In addition, the TGF-β antagonists may be incorporated into biodegradable polymers allowing for sustained release of the compound, the polymers being implanted in the vicinity of where drug delivery is desired, for example, at the site of a tumor or implanted so that the TGF-β antagonist is slowly released systemically. Osmotic minipumps may also be used to provide controlled delivery of high concentrations of the TGF-β antagonists through cannulae to the site of interest, such as directly into a metastatic growth or into the vascular supply to that tumor. The biodegradable polymers and their use are described, for example, in detail in Brem et al. (1991, J Neurosurg 74, 441–446), which is hereby incorporated by reference in its entirety.

The compositions containing a polypeptide of this invention can be administered intravenously, as by injection of a unit dose, for example. The term "unit dose" when used in reference to a therapeutic composition of the present invention refers to physically discrete units suitable as unitary dosage for the subject, each unit containing a predetermined quantity of active material calculated to produce the desired therapeutic effect in association with the required diluent; i.e., carrier or vehicle.

Modes of administration of the compositions of the present inventions include intravenous, intramuscular, intraperitoneal, intrasternal, subcutaneous and intraarticular injection and infusion. Pharmaceutical compositions for parenteral injection comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyois (e.g., glycerol, propylene glycol, polyethylene glycol and the like), carboxymethylcellulose and suitable mixtures thereof, vegetable oils (e.g., olive oil) and injectable organic esters such as ethyl oleate. Proper fluidity may be maintained, for example, by the use of coating materials such as lecithin, by the maintenance of the required particle size in the case of dispersions and by the use of surfactants. These compositions may also contain adjuvants such as preservatives, wetting agents, emulsifying agents and dispersing agents. Prevention of the action of microorganisms may be ensured by the inclusion of various antibacterial and antifungal agents such as paraben, chlorobutanol, phenol sorbic acid and the like. It may also be desirable to include isotonic agents such as sugars, sodium chloride and the like. Prolonged absorption of the injectable pharmaceutical form may be brought about by the inclusion of agents, such as aluminum monostearate and gelatin, which delay absorption. Injectable depot forms are made by forming microencapsule matrices of the drug in biodegradable polymers such as polylactide-polyglycolide, poly (orthoesters) and poly(anhydrides). Depending upon the ratio of drug to polymer and the nature of the particular polymer employed, the rate of drug release can be controlled. Depot injectable formulations are also prepared by entrapping the drug in liposomes or microemulsions which are compatible with body tissues. The injectable formulations may be sterilized, for example, by filtration through a bacterial-retaining filter or by incorporating sterilizing agents in the form of sterile solid compositions which can be dissolved or dispersed in sterile water or other sterile injectable media just prior to use.

The therapeutic compositions of the present invention can include pharmaceutically acceptable salts of the components therein, e.g., which may be derived from inorganic or organic acids. By "pharmaceutically acceptable salt" is meant those salts which are, within the scope of sound medical judgement, suitable for use in contact with the tissues of humans and lower animals without undue toxicity, irritation, allergic response and the like and are commensurate with a reasonable benefit/risk ratio. Pharmaceutically acceptable salts are well-known in the art. For example, S. M. Berge, et al. describe pharmaceutically acceptable salts in detail in *J. Pharmaceutical Sciences* (1977) 66:1 et seq., which is incorporated herein by reference. Pharmaceutically acceptable salts include the acid addition salts (formed with the free amino groups of the polypeptide) that are formed with inorganic acids such as, for example, hydrochloric or phosphoric acids, or such organic acids as acetic, tartaric, mandelic and the like. Salts formed with the free carboxyl groups can also be derived from inorganic bases such as, for example, sodium, potassium, ammonium, calcium or ferric hydroxides, and such organic bases as isopropylamine, trimethylamine, 2-ethylamino ethanol, histidine, procaine and the like. The salts may be prepared in situ during the final isolation and purification of the compounds of the invention or separately by reacting a free base function with a suitable organic acid. Representative acid addition salts include, but are not limited to acetate, adipate, alginate, citrate, aspartate, benzoate, benzenesulfonate, bisulfate, butyrate, camphorate, camphorsufonate, digluconate, glycerophosphate, hemisulfate, heptonoate, hexanoate, fumarate, hydrochloride, hydrobromide, hydroiodide, 2-hydroxymethanesulfonate (isethionate), lactate, maleate, methanesulfonate, nicotinate, 2-naphthalenesulfonate, oxalate, pamoate, pectinate, persulfate, 3-phenylpropionate, picrate, pivalate, propionate, succinate, tartate, thiocyanate, phosphate, glutamate, bicarbonate, p-toluenesulfonate and undecanoate. Also, the basic nitrogen-containing groups can be quaternized with such agents as lower alkyl halides such as methyl, ethyl, propyl, and butyl chlorides, bromides and iodides; dialkyl sulfates like dimethyl, diethyl, dibutyl, and diamyl sulfates; long chain halides such as decyl, lauryl, myristyl and stearyl chlorides, bromides and iodides; arylalkyl halides like benzyl and phenethyl bromides and others. Water or oil-soluble or dispersible products are thereby obtained. Examples of acids which may be employed to form pharmaceutically acceptable acid addition salts include such inorganic acids as hydrochloric acid, hydrobromic acid, sulphuric acid and phosphoric acid and such organic acids as oxalic acid, maleic acid, succinic acid and citric acid.

As used herein, the terms "pharmaceutically acceptable," "physiologically tolerable" and grammatical variations thereof as they refer to compositions, carriers, diluents and reagents, are used interchangeably and represent that the materials are capable of administration to or upon a mammal with a minimum of undesirable physiological effects such as nausea, dizziness, gastric upset and the like. The preparation of a pharmacological composition that contains active ingredients dissolved or dispersed therein is well understood in the art and need not be limited based on formulation. Typically such compositions are prepared as injectables either as liquid solutions or suspensions, however, solid forms suitable for solution, or suspensions, in liquid prior to use can also be prepared. The preparation can also be emulsified.

The active ingredient can be mixed with excipients which are pharmaceutically acceptable and compatible with the active ingredient and in amounts suitable for use in the therapeutic methods described herein. Suitable excipients include, for example, water, saline, dextrose, glycerol, ethanol or the like and combinations thereof. In addition, if desired, the composition can contain minor amounts of auxiliary substances such as wetting or emulsifying agents, pH buffering agents and the like which enhance the effectiveness of the active ingredient.

The TGF-$\beta$ antagonist of the present invention can also be included in a composition comprising a prodrug. As used herein, the term "prodrug" refers to compounds which are rapidly transformed in vivo to yield the parent compound, for example, by enzymatic hydrolysis in blood. A thorough discussion is provided in T. Higuchi and V. Stella, *Prodrugs as Novel Delivery Systems,* Vol. 14 of the ACS Symposium Series and in Edward B. Roche, ed., *Bioreversible Carriers in Drug Design,* American Pharmaceutical Association and Permagon Press, 1987, both of which are incorporated herein by reference. As used herein, the term "pharmaceutically acceptable prodrug" refers to (1) those prodrugs of the compounds of the present invention which are, within the scope of sound medical judgement, suitable for use in contact with the tissues of humans and animals without undue toxicity, irritation, allergic response and the like, commensurate with a suitable benefit-to-risk ratio and effective for their intended use and (2) zwitterionic forms, where possible, of the parent compound.

The dosage of the TGF-$\beta$ antagonist of the present invention will depend on the disease state or condition being treated and other clinical factors such as weight and condition of the human or animal and the route of administration of the compound. For treating humans or animals, about 1 $\mu$g/kg of body weight to about 50 mg/kg of body weight can be administered, preferably about 1 mg/kg of body weight to about 20 mg/kg of body weight. Preferably the dosage is about 5 mg/kg, e.g., as when antibodies were used in the experiments depicted in FIG. 4A. In combination therapies, e.g., the protein(s) of the invention in combination with radiotherapy, chemotherapy, or immunotherapy, it may be possible to reduce the dosage, twofold to twentyfold, e.g., to about 0.1 mg/kg of body weight to about 0.2 mg/kg of body weight. Depending upon the half-life of the TGF-$\beta$ antagonist in the particular animal or human, the TGF-$\beta$ antagonist can be administered between several times per day to once a week. It is to be understood that the present invention has application for both human and veterinary use. The methods of the present invention contemplate single as well as multiple administrations, given either simultaneously or over an extended period of time. In addition, the TGF-$\beta$ antagonist can be administered in conjunction with other forms of therapy, e.g., chemotherapy, radiotherapy, or immunotherapy.

The TGF-$\beta$ antagonist formulations include those suitable for oral, rectal, ophthalmic (including intravitreal or intracameral), nasal, topical (including buccal and sublingual), intrauterine, vaginal or parenteral (including subcutaneous, intraperitoneal, intramuscular, intravenous, intradermal, intracranial, intratracheal, and epidural) administration. The TGF-$\beta$ antagonist formulations may conveniently be presented in unit dosage form and may be prepared by conventional pharmaceutical techniques. Such techniques include the step of bringing into association the active ingredient and the pharmaceutical carrier(s) or excipient(s). In general, the formulations are prepared by uniformly and intimately bringing into association the active ingredient with liquid carriers or finely divided solid carriers or both, and then, if necessary, shaping the product.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in a freeze-dried (lyophilized) condition requiring only the addition of the sterile liquid carrier, for example, water for injections, immediately prior to use. Extemporaneous injection solutions and suspensions may be prepared from sterile powders, granules and tablets of the kind previously described.

When an effective amount of the TGF-β antagonist of the present invention is administered orally, the TGF-β antagonist of the present invention will be in the form of a tablet, capsule, powder, solution or elixir. When administered in tablet form, the pharmaceutical composition of the invention may additionally contain a solid carrier such as a gelatin or an adjuvant. The tablet, capsule, and powder contain from about 5 to 95% protein of the present invention, and preferably from about 25 to 90% protein of the present invention. When administered in liquid form, a liquid carrier such as water, petroleum, oils of animal or plant origin such as peanut oil, mineral oil, soybean oil, or sesame oil, or synthetic oils may be added. The liquid form of the pharmaceutical composition may further contain physiological saline solution, dextrose or other saccharide solution, or glycols such as ethylene glycol, propylene glycol or polyethylene glycol. When administered in liquid form, the pharmaceutical composition contains from about 0.5 to 90% by weight of protein of the present invention, and preferably from about 1 to 50% protein of the present invention.

When an effective amount of TGF-β antagonist of the present invention is administered by intravenous, cutaneous or subcutaneous injection, TGF-β antagonist of the present invention will be in the form of a pyrogen-free, parenterally acceptable aqueous solution. The preparation of such parenterally acceptable TGF-β antagonist solutions, having due regard to pH, isotonicity, stability, and the like, is within the skill in the art. A preferred pharmaceutical composition for intravenous, cutaneous, or subcutaneous injection should contain, in addition to TGF-β antagonist of the present invention, an isotonic vehicle such as Sodium Chloride Injection, Ringer's Injection, Dextrose Injection, Dextrose and Sodium Chloride Injection, Lactated Ringer's Injection, or other vehicle as known in the art. The pharmaceutical composition of the present invention may also contain stabilizers, preservatives, buffers, antioxidants, or other additives known to those of skill in the art.

The amount of TGF-β antagonist of the present invention in the pharmaceutical composition of the present invention will depend upon the nature and severity of the condition being treated, and on the nature of prior treatments which the patient has undergone. Ultimately, the attending physician will decide the amount of TGF-β antagonist of the present invention with which to treat each individual patient. Initially, the attending physician will administer low doses of TGF-β antagonist of the present invention and observe the patient's response. Larger doses of TGF-β antagonist of the present invention may be administered until the optimal therapeutic effect is obtained for the patient, and at that point the dosage is not increased further.

The duration of intravenous therapy using the pharmaceutical composition of the present invention will vary, depending on the severity of the disease being treated and the condition and potential idiosyncratic response of each individual patient. It is contemplated that the duration of each application of the TGF-β antagonist of the present invention will be in the range of 12 to 24 hours of continuous intravenous administration. Ultimately the attending physician will decide on the appropriate duration of intravenous therapy using the pharmaceutical composition of the present invention.

Preferred unit dosage formulations are those containing a daily dose or unit, daily sub-dose, or an appropriate fraction thereof, of the administered ingredient. It should be understood that in addition to the ingredients, particularly mentioned above, the formulations of the present invention may include other agents conventional in the art having regard to the type of formulation in question. Optionally, cytotoxic agents may be incorporated or otherwise combined with the TGF-β, or biologically functional protein fragments thereof, to provide dual therapy to the patient.

The therapeutic compositions are also presently valuable for veterinary applications. Particularly domestic animals and thoroughbred horses, in addition to humans, are desired patients for such treatment with the present invention.

Cytotoxic agents such as ricin, can be linked to the TGF-β, and fragments thereof, thereby providing a tool for destruction of cells that bind the TGF-β. These cells may be found in many locations, including but not limited to, micrometastases and primary tumors. Proteins linked to cytotoxic agents are infused in a manner designed to maximize delivery to the desired location. For example, ricin-linked high affinity fragments are delivered through a cannula into vessels supplying the target site or directly into the target. Such agents are also delivered in a controlled manner through osmotic pumps coupled to infusion cannulae. A combination of antagonists to the TGF-β may be co-applied with stimulators of angiogenesis to increase vascularization of tissue. This therapeutic regimen provides an effective means of destroying metastatic cancer.

Additional treatment methods include administration of the TGF-β, fragments, analogs, antisera, or receptor agonists and antagonists thereof, linked to cytotoxic agents. It is to be understood that the TGF-β can be human or animal in origin. The TGF-β can also be produced synthetically by chemical reaction or by recombinant techniques in conjunction with expression systems.

The present invention also encompasses gene therapy whereby a polynucleotide encoding the TGF-β, or a mutant, fragment, or fusion protein thereof, or other molecule designed to antagonize TGF-β action, is introduced and regulated in a patient. Alternatively, a polynucleotide encoding an antibody to TGF-β may be employed. Various methods of transferring or delivering DNA to cells for expression of the gene product protein, otherwise referred to as gene therapy, are disclosed in *Gene Transfer into Mammalian Somatic Cells* in vivo, N. Yang (1992) *Crit. Rev. Biotechn.* 12(4):335–356, which is hereby incorporated by reference. Gene therapy encompasses incorporation of DNA sequences into somatic cells or germ line cells for use in either ex vivo or in vivo therapy. Gene therapy functions to replace genes, augment normal or abnormal gene function, and to combat infectious diseases and other pathologies.

Strategies for treating these medical problems with gene therapy include therapeutic strategies such as identifying the defective gene and then adding a functional gene to either replace the function of the defective gene or to augment a slightly functional gene; or prophylactic strategies, such as adding a gene for the product protein that will treat the condition or that will make the tissue or organ more susceptible to a treatment regimen. As an example of a prophylactic strategy, a polynucleotide such as that encoding a TGF-β antagonist may be placed in a patient and thus prevent occurrence of angiogenesis; or a gene that makes tumor cells more susceptible to radiation could be inserted and then radiation of the tumor would cause increased killing of the tumor cells.

Many protocols for transfer of the DNA or regulatory sequences of the TGF-β are envisioned in this invention. Transfection of promoter sequences, other than one normally found specifically associated with the TGF-β, or other sequences which would increase production of the TGF-β are also envisioned as targets of gene therapy. An example of this technology is found in Transkaryotic Therapies, Inc., of Cambridge, Mass., using homologous recombination to insert a "genetic switch" that turns on an erythropoietin gene in cells. See *Genetic Engineering News*, Apr. 15, 1994. Such "genetic switches" could be used to inactivate the TGF-β (or receptors) in cells not normally expressing that protein (or receptors).

Gene transfer methods for gene therapy fall into three broad categories: physical (e.g., electroporation, direct gene transfer and particle bombardment), chemical (e.g., lipid-based carriers, or other non-viral vectors) and biological (e.g., virus-derived vector and receptor uptake). For example, non-viral vectors may be used which include liposomes coated with DNA. Such liposome/DNA complexes may be directly injected intravenously into the patient. It is believed that the liposome/DNA complexes are concentrated in the liver where they deliver the DNA to macrophages and Kupffer cells. These cells are long lived and thus provide long term expression of the delivered DNA. Additionally, vectors or the "naked" DNA of the gene may be directly injected into the desired organ, tissue or tumor for targeted delivery of the therapeutic DNA.

Gene therapy methodologies can also be described by delivery site. Fundamental ways to deliver genes include ex vivo gene transfer, in vivo gene transfer, and in vitro gene transfer. In ex vivo gene transfer, cells are taken from the patient and grown in cell culture. The DNA is transfected into the cells, the transfected cells are expanded in number and then reimplanted in the patient. In in vitro gene transfer, the transformed cells are cells growing in culture, such as tissue culture cells, and not particular cells from a particular patient. These "laboratory cells" are transfected, the transfected cells are selected and expanded for either implantation into a patient or for other uses.

In vivo gene transfer involves introducing the DNA into the cells of the patient when the cells are within the patient. Methods include using virally mediated gene transfer using a noninfectious virus to deliver the gene in the patient or injecting naked DNA into a site in the patient and the DNA is taken up by a percentage of cells in which the gene product protein is expressed. Additionally, the other methods described herein, such as use of a "gene gun," may be used for in vitro insertion of the DNA or regulatory sequences controlling production of the TGF-β.

Chemical methods of gene therapy may involve a lipid based compound, not necessarily a liposome, to transfer the DNA across the cell membrane. Lipofectins or cytofectins, lipid-based positive ions that bind to negatively charged DNA, make a complex that can cross the cell membrane and provide the DNA into the interior of the cell. Another chemical method uses receptor-based endocytosis, which involves binding a specific ligand to a cell surface receptor and enveloping and transporting it across the cell membrane. The ligand binds to the DNA and the whole complex is transported into the cell. The ligand gene complex is injected into the blood stream and then target cells that have the receptor will specifically bind the ligand and transport the ligand-DNA complex into the cell.

Many gene therapy methodologies employ viral vectors to insert genes into cells. For example, altered retrovirus vectors have been used in ex vivo methods to introduce genes into peripheral and tumor-infiltrating lymphocytes, hepatocytes, epidermal cells, myocytes, or other somatic cells. These altered cells are then introduced into the patient to provide the gene product from the inserted DNA.

Viral vectors have also been used to insert genes into cells using in vivo protocols. To direct the tissue-specific expression of foreign genes, cis-acting regulatory elements or promoters that are known to be tissue-specific can be used. Alternatively, this can be achieved using in situ delivery of DNA or viral vectors to specific anatomical sites in vivo. For example, gene transfer to blood vessels in vivo was achieved by implanting in vitro transduced endothelial cells in chosen sites on arterial walls. The virus infected surrounding cells which also expressed the gene product. A viral vector can be delivered directly to the in vivo site, by a catheter for example, thus allowing only certain areas to be infected by the virus, and providing long-term, site specific gene expression. In vivo gene transfer using retrovirus vectors has also been demonstrated in mammary tissue and hepatic tissue by injection of the altered virus into blood vessels leading to the organs.

Viral vectors that have been used for gene therapy protocols include but are not limited to, retroviruses, other RNA viruses such as poliovirus or Sindbis virus, adenovirus, adeno-associated virus, herpes viruses, SV 40, vaccinia and other DNA viruses. Replication-defective murine retroviral vectors are the most widely utilized gene transfer vectors. Murine leukemia retroviruses are composed of a single strand RNA complexed with a nuclear core protein and polymerase (pol) enzymes, encased by a protein core (gag) and surrounded by a glycoprotein envelope (env) that determines host range. The genomic structure of retroviruses include the gag, pol, and env genes enclosed at by the 5' and 3' long terminal repeats (LTR). Retroviral vector systems exploit the fact that a minimal vector containing the 5' and 3' LTRs and the packaging signal are sufficient to allow vector packaging, infection and integration into target cells providing that the viral structural proteins are supplied in trans in the packaging cell line. Fundamental advantages of retroviral vectors for gene transfer include efficient infection and gene expression in most cell types, precise single copy vector integration into target cell chromosomal DNA, and ease of manipulation of the retroviral genome.

The adenovirus is composed of linear, double stranded DNA complexed with core proteins and surrounded with capsid proteins. Advances in molecular virology have led to the ability to exploit the biology of these organisms to create vectors capable of transducing novel genetic sequences into target cells in vivo. Adenoviral-based vectors will express gene product proteins at high levels. Adenoviral vectors have high efficiencies of infectivity, even with low titers of virus. Additionally, the virus is fully infective as a cell free virion so injection of producer cell lines are not necessary. Another potential advantage to adenoviral vectors is the ability to achieve long term expression of heterologous genes in vivo.

Mechanical methods of DNA delivery include fusogenic lipid vesicles such as liposomes or other vesicles for membrane fusion, lipid particles of DNA incorporating cationic lipid such as lipofectin, polylysine-mediated transfer of DNA, direct injection of DNA, such as microinjection of DNA into germ or somatic cells, pneumatically delivered DNA-coated particles, such as the gold particles used in a "gene gun," and inorganic chemical approaches such as calcium phosphate transfection. Particle-mediated gene transfer methods were first used in transforming plant tissue. With a particle bombardment device, or "gene gun," a motive force is generated to accelerate DNA-coated high density particles (such as gold or tungsten) to a high velocity that allows penetration of the target organs, tissues or cells. Particle bombardment can be used in in vitro systems, or with ex vivo or in vivo techniques to introduce DNA into cells, tissues or organs. Another method, ligand-mediated gene therapy, involves complexing the DNA with specific ligands to form ligand-DNA conjugates, to direct the DNA to a specific cell or tissue.

It has been found that injecting plasmid DNA into muscle cells yields high percentage of the cells which are transfected and have sustained expression of marker genes. The DNA of the plasmid may or may not integrate into the genome of the cells. Non-integration of the transfected DNA would allow the transfection and expression of gene product proteins in terminally differentiated, non-proliferative tissues for a prolonged period of time without fear of mutational insertions, deletions, or alterations in the cellular or mitochondrial genome. Long-term, but not necessarily permanent, transfer of therapeutic genes into specific cells may provide treatments for genetic diseases or for prophylactic use. The DNA could be reinjected periodically to maintain the gene product level without mutations occurring in the genomes of the recipient cells. Non-integration of exogenous DNAs may allow for the presence of several different exogenous DNA constructs within one cell with all of the constructs expressing various gene products.

Electroporation for gene transfer uses an electrical current to make cells or tissues susceptible to electroporation-mediated mediated gene transfer. A brief electric impulse with a given field strength is used to increase the permeability of a membrane in such a way that DNA molecules can penetrate into the cells. This technique can be used in in vitro systems, or with ex vivo or in vivo techniques to introduce DNA into cells, tissues or organs.

Carrier mediated gene transfer in vivo can be used to transfect foreign DNA into cells. The carrier-DNA complex can be conveniently introduced into body fluids or the bloodstream and then site-specifically directed to the target organ or tissue in the body. Both liposomes and polycations, such as polylysine, lipofectins or cytofectins, can be used. Liposomes can be developed which are cell specific or organ specific and thus the foreign DNA carried by the liposome will be taken up by target cells. Injection of immunoliposomes that are targeted to a specific receptor on certain cells can be used as a convenient method of inserting the DNA into the cells bearing the receptor. Another carrier system that has been used is the asialoglycoportein/polylysine conjugate system for carrying DNA to hepatocytes for in vivo gene transfer.

The transfected DNA may also be complexed with other kinds of carriers so that the DNA is carried to the recipient cell and then resides in the cytoplasm or in the nucleoplasm. DNA can be coupled to carrier nuclear proteins in specifically engineered vesicle complexes and carried directly into the nucleus.

Gene regulation of the TGF-β may be accomplished by administering compounds that bind to the gene encoding one of the TGF-β, or control regions associated with the gene, or its corresponding RNA transcript to modify the rate of transcription or translation. Additionally, cells transfected with a DNA sequence encoding the TGF-β antagonist may be administered to a patient to provide an in vivo source of that protein. For example, cells may be transfected with a vector containing a nucleic acid sequence encoding the TGF-β antagonist. The transfected cells may be cells derived from the patient's normal tissue, the patient's diseased tissue, or may be non-patient cells.

For example, tumor cells removed from a patient can be transfected with a vector capable of expressing the TGF-β antagonist of the present invention, and re-introduced into the patient. The transfected tumor cells produce levels of the TGF-β antagonist in the patient that inhibit the growth of the tumor. Patients may be human or non-human animals. Cells may also be transfected by non-vector, or physical or chemical methods known in the art such as electroporation, ionoporation, or via a "gene gun." Additionally, the DNA may be directly injected, without the aid of a carrier, into a patient. In particular, the DNA may be injected into skin, muscle or blood.

The gene therapy protocol for transfecting the TGF-β antagonist into a patient may either be through integration of the TGF-β antagonist DNA into the genome of the cells, into minichromosomes or as a separate replicating or non-replicating DNA construct in the cytoplasm or nucleoplasm of the cell. Expression of the TGF-β antagonist may continue for a long-period of time or may be reinjected periodically to maintain a desired level of the protein(s) in the cell, the tissue or organ or a determined blood level.

Anti-sense oligonucleotides that bind to DNA and RNA that encode TGF-β can also be used to inhibit the expression of TGF-β, and thus, inhibit TGF-β activity. For example, the nucleotide sequence of TGF-β is known, and has been deposited in Genbank, and anti-sense oligos can therefore be designed to inhibit the secretion of TGF-β. Other molecules that inhibit extracellular absorption and action of TGF-β can also be used, as well as molecules that bind the TGF-β receptors, or prevent the conversion of the latent to the active form of TGF-β, or antisense molecules that prevent TGF-β secretion, or inactivate the intracellular sites within cells that bind TGF-β, or prevent the autoregulation (induction) of TGF-β, are also encompassed by the present invention.

Also encompassed in the present invention are methods of combination therapy where the TGF-β inhibitory molecules contact the proliferating cells in combination with one, or more, additional anti-angiogenic molecules. TGF-β is believed to inhibit angiogenesis at the resolution phase of vessel formation, which is why previous studies have attempted to inhibit angiogenesis by administration of TGF-β. In particular, these anti-angiogenic molecules can inhibit angiogenesis at the same phase, or at a different phase of vessel formation. For instance, since endostatin seems to inhibit the initiation phase of angiogenesis (i.e., cell proliferation and migration), whereas TGF-β is important in the resolution phase, it may be that endostatin in combination with methods to neutralize TGF-β activity may be additive or synergistic. Other anti-angiogenic proteins that work in the same or other phases of angiogenesis can also be used in conjunction with the present invention, including angiostatin, endostatin, restin, apomigren, Arresten, Canstatin, or Tumstatin, which are described above.

The combination of TGF-β inhibitors and anti-angiogenic molecules can be administered substantially simultaneously, or sequentially. The timing of administering these molecules to the vertebrate can be determined empirically using techniques well-known to those of skill in the art. The combination therapy described herein specifically results in the inhibition of proliferation of tumors, (e.g., no new tumor growth, or increase in tumor size) or in the regression of an established tumor (e.g., a detectable decrease in tumor size).

Another embodiment of the present invention encompasses a combination therapy where the TGF-β inhibitors are administered in combination with chemotherapy, immunotherapy or radiation therapy. In particular, the administration of TGF-β inhibitors can augment, or enhance, the effects of the chemotherapeutic, immunologic or radiologic agent. Examples of such methods are described by Mauceri, H., et al. (*Nature* 394, 287–291(1998)).

The present invention also encompasses methods of inhibiting tumor metastasis by inhibiting the angiogenic activity of TGF-β, in particular where the tumor cells secrete TGF-β. For example, many tumors require angiogenesis in order to grow and metastasize. By inhibiting the ability of these tumors to promote angiogenesis, metastasis can also be inhibited. In particular, if the tumor cells secrete TGF-β, the inhibition of TGF-β-mediated angiogenesis can inhibit tumor metastasis.

Alternatively, by measuring the levels of TGF-β in a biological sample obtained from the vertebrate, it can be determined if the tumor is metastisizing. For example, an increase (i.e., elevation over normal levels (3.99±0.77 ng/ml (Ivanovic, I. et al., *Nat Med* 1, 282–283, 1995)) of TGF-β in blood, plasma, serum, urine or in a tissue biopsy sample is indicative of tumor metastesis. TGF-β levels can be measured by standard radioimmunoassays.

Further encompassed by the present invention are methods of evaluating the efficacy of an anti-tumor therapy that comprises the use of TGF-β inhibitors of the present invention. As described herein, tumors can comprise cells that secrete TGF-β, and the secreted TGF-β can stimulate angiogenesis whether or not functional TGF-β receptors are also present on the tumor cell surface. If the receptor is expressed on the cell surface, and if it is functional, then TGF-β can inhibit tumor cell proliferation. However, if the receptor is not expressed, or it is not functional (e.g., does not bind TGF-β) then the secreted TGF-β can stimulate angiogenesis. The present invention encompasses the evaluation of tumor cells for the expression of the TGF-β receptor. Methods of measuring expression of such TGF-β receptors have been described, e.g., by Goggins, M. et al. (*Cancer Res* 58, 5329–5332 (1998)). If the receptor is expressed and is functional, therapy of choice can include administering to the vertebrate TGF-β, or a biologically active fragment, analog, homolog, mutant, derivative or mimic thereof, in an amount sufficient to bind to the TGF-β receptor to result in the inhibition of tumor growth, or in the regression of tumor size. If the receptor is not expressed or is not able to bind TGF-β, then the therapy of choice can include administering to the vertebrate a TGF-β inhibitor molecule, as described herein, in an amount sufficient to inhibit the TGF-β-mediated angiogenic activity, which results in the inhibition of tumor growth, or in the regression of tumor size.

As described in detail in the Examples below, anti-TGF-β therapy regressed established tumors. In 4 out of 10 treated animals, tumors diminished to a size of about 50 mm³, reminiscent of the "rests" seen after therapy with endostatin, an approximately 20 kDa antiangiogenic C terminus fragment of collagen XVIII (Boehm, T., Folkman, J., Browder, T. & O'Reilly, M. S., *Nature* 390, 404–407 (1997), and O'Reilly, M. S. et al., *Cell* 88, 277–285 (1997)). As with endostatin, the tumors quickly regrew upon cessation of therapy, and could again be treated successfully. These data demonstrate the lack of drug resistance but highlight the need for either chronic therapy or for multimodality therapy (see below) to effect inhibition.

Additionally, on a molar basis, anti-TGF antibody was about 60 times more effective than endostatin, based on published data non-RCC data (O'Reilly, M. S. et al., *Cell* 79, 315–328 (1994)). This number could be further increased with a higher affinity antibody, or one with improved pharmacokinetics. Since endostatin appears to inhibit the initiation phase of angiogenesis (cell proliferation and migration) whereas TGF-β1 is important in the resolution phase, it is conceivable that endostatin in combination with methods to neutralize TGF-β1 activity may be additive or synergistic. Similarly, TGF-β1 neutralization in combination with chemotherapy, immunotherapy, or radiation makes eminent sense. Also, it is noteworthy that the acquisition of TGF-β1 unresponsiveness correlates well with tumor progression (Ramp, U. et al., *Lab Invest* 4976, 739–749 (1997), Sehgal, I., Baley, P. A. & Thompson, T. C., *Cancer Res* 56, 3359–3365 (1996) and Filmus, J. & Kerbel, R. S., *Curr Opin Oncol* 5, 123–129 (1993)), so that anti-TGFβ1 therapy will be the most useful in advanced disease when other modalities are less likely to be effective.

There is the possibility that TGF-β1 induced by the process of surgery itself (Fisher, F. & Fisher, E. R., *Science* 130, 918–919 (1959)) or by radiation (Parker, C. C. & Yarnold, J. R., *Clin Oncol (R Coll Radiol)* 7, 160–161 (1995)) may stimulate metastatic growth especially if the metastatic lesions are resistant to TGF-β's growth inhibitory activity (Sehgal, I., Baley, P. A. & Thompson, T. C., *Cancer Res* 56, 3359–3365 (1996)). Along these lines O'Reilly and Folkman have shown that a combination of TGF-β1 and bFGF administered systemically can cause the regrowth of small tumor "rests" following endostatin therapy (O'Reilly, M. S., In: *IBC Conference*, Boston, 1998). These data point to the potential importance of monitoring TGF-β1 levels in a cancer patient, assessing tumor profiling of TGF-β and its receptors and suggests the possible use of anti-TGF-β therapy either at the time of primary tumor removal, or at surgery in a patient with cancer in remission or pre- and peri-radiation therapy. Finally, other approaches to negating TGF-β1's effect may be more efficacious or practical than the use of neutralizing antibody. Decorin, a proteoglycan known to bind TGF-β (Santra, M., Skorski, T., Calabretta, B., Lattime, E. C. & Iozzo, R. V., *Proc Natl Acad Sci USA* 92, 7016–7020 (1995)), latency associated peptide (LAP), soluble TGF-β receptors, antisense oligonucleotides, TGF-β peptide antagonists (Huang, S. S., Liu, Q., Johnson, F. E., Konish, Y. & Huang, J. S., *J Biol Chem* 272, 27155–27159 (1997)), and drugs working intracellularly on TGF-β-induced signalling can also be used to inhibit TGF-β activity.

As described herein, it is now demonstrated shown that TGF-β1 is a target for the VHL tumor suppressor gene product and that repression of TGF-β1 message occurs predominantly at a post-transcriptional level. Identification of potential RNA binding proteins and destabilizing elements in the TGF-β1 mRNA will help elucidate the function of pVHL. Whereas VHL mutations occurs early in RCC development, an important secondary genetic event in the TGF-β1 signaling pathway leads to abrogation of TGF-β type II receptor expression and resistance to the antiproliferative effects of TGF-β1. Moreover, as demonstrated herein, the biological significance of elevated TGF-β1 in RCCs is to stimulate angiogenesis, and that neutralizing TGF-β activity can regress established RCCs without the development of drug resistance. Thus, blocking the paracrine effects of TGF-β1 can provide novel strategies for RCCs and other cancer cells that secrete TGF-β1, as well as stromal cells, fibroblasts, macrophages, platelets, endothelial calls, granular neutrophils, and other cells that secrete TGF-β.

The invention is further illustrated by the following examples, which are not meant to be construed in any way as imposing limitations upon the scope thereof. On the contrary, it is to be clearly understood that resort may be had to various other embodiments, modifications, and equivalents thereof, which, after reading the description herein, may suggest themselves to those skilled in the art without departing from the spirit of the present invention and/or the scope of the appended claims.

EXAMPLES

Example 1

Methods

Plasmids and Cell Culture

RCC cells (786-O from ATCC (American Type Culture Collection, 10801 University Boulevard, Manassas, Va., 20110-2209, USA), lacking the wt VHL gene 26 were stably transfected (Iliopoulos, O., Kibel, A., Gray, S. & Kaelin, W. G., Jr., Nat Med 1, 822–826 (1995)), with an expression vector containing full length VHL cDNA epitope—tagged in the N-terminus with FLAG sequence (pCMV2-FlagVHL) as described in (Knebelmann, B., Ananth, S., Cohen, H. T. & Sukhatme, V. P., Cancer Res 58, 226–231 (1998) and Mukhopadhyay, D., Knebelmann, B., Cohen, H. T., Ananth, S. & Sukhatme, V. P., Mol Cell Biol 17, 5629–5639 (1997)). 786-O clonal cell lines stably transfected with either pRC (786-O Neo), pRC-HAVHL (786-O HA VHL) and pRC-HAVHL (1–115) which lacks a 116–213 (786-O HA ΔVHL) were gifts from W. Kaelin and have been described previously (Iliopoulos, 0., Kibel, A., Gray, S. & Kaelin, W. G., Jr., Nat Med 1, 822–826 (1995)). 786-O Flag VHL, 786-O Neo, 786-O HA VHL, 786-O HA ΔVHL were grown in DMEM with 10% FBS and supplemented with G418. Wild type 786-O and CCL-64 (mink lung epithelial cells) were grown in DMEM with 10% FBS.

RNA Extraction and Northern Blot Analysis

These experiments were done as described previously (Mukhopadhyay, D., Knebelmann, B., Cohen, H. T., Ananth, S. & Sukhatme, V. P., Mol Cell Biol 17, 5629–5639 (1997)). The probes used were a TGF-β1 2.1 kb EcoRI fragment (phTGTB-2 from ATCC and a 600 bp PCR amplified fragment from human actin cDNA.

ELISA Analysis of TGF-β1 Secretion

ELISA of cell culture supernatants obtained from confluent cultures was performed using the manufacturer's recommended procedures (Quantakine kit from R&D Systems, Minneapolis, Minn., USA). All samples and standards were run in triplicate. Color intensity was measured at 450 nm using a spectrophoretic plate reader. Activation of latent TG-β to imununoreactive TGFβ1 was performed according to the manufacturer's recommendations and all samples were measured before (active TGF-β1) and after activation (latent TGF-β1).

Western Blot Analysis

Cells were grown to 70%–80% confluence and lysed in lysis buffer as previously described (Knebelmann, B., Ananth, S., Cohen, H. T. & Sukhatme, V. P., Cancer Res 58, 226–231 (1998) and Mukhopadhyay, D., Knebelmann, B., Cohen, H. T., Ananth, S. & Sukhatme, V. P., Mol Cell Biol 17, 5629–5639 (1997)). Equal amounts of cell lysates (50 ug) as determined by Bradford assay were loaded. Antibodies included TGF-β type I1 receptor specific Ab (Santa Cruz, Calif.), actin Ab (Santa Cruz, Calif.) and VHL Ab (gift of W. Kaelin).

Nuclear Run-on In Vitro Transcription Assay

Nuclei isolation and in vitro transcription were performed as described previously (Knebelmann, B., Ananth, S., Cohen, H. T. & Sukhatme, V. P., Cancer Res 58, 226–231 (1998) and Mukhopadhyay, D., Knebelmann, B., Cohen, H. T., Ananth, S. & Sukhatme, V. P., Mol Cell Biol 17, 5629–5639 (1997)). Probes were either gel purified inserts from plasmids or were generated by PCR. The TGF-β1 probe used (about 2 kb) contained the entire coding region of TGF-β1, including 779 bp of 5' untranslated, and 216 bp of 3' untranslated sequence. The amount of sample hybridizing to the TG-β probe was normalized by dividing the TG-β signal by that of GAPDH within each experiment.

Actinomycin-D Experiments

These experiments were performed as described previously (Knebelmann, B., Ananth, S., Cohen, H. T. & Sukhatme, V. P., Cancer Res 58, 226–231 (1998)). Briefly, subconfluent cells were exposed to 5 μg/ml Actinomycin-D (Sigma Chemical Co., St. Louis, Mo., USA) from 0–24 hrs. Total RNA was isolated from 786-O cells and signal on northern blot analysis determined for TGF-β1 after normalization for RNA loading and transfer using the 28S band on the transferred membrane.

Assessment of growth properties after exposure to TGF-β1:

DNA synthesis was studied in triplicate by $^3$H-thymidine incorporation into DNA. Two thousand cells were plated in 24 well plates in DMEM with 0.5% FBS. Twenty-four hours after plating, the medium was replaced with or without TGF-β1 (1 ng/ml or 10 ng/ml from R&D Systems) and anti-TGF-β1,-β2,-β3 monoclonal antibody (10 μg/ml from Genzyme Diagnostics (Cambridge, Mass., USA)) for 48 hours. In vitro and in vivo neutralization of this TGF-β antibody has been published (Ayala, A., Meldrum, D. R., Perrin, M. M. & Chaudry, I. H., Immunology 79, 479–484 (1993), Tzai, T. S., Shiau, A. L., Lin, C. S., Wu, C. L. & Lin, J. S., Anticancer Res 17, 1073–1078 (1997), and Riser, B. L. et al., J Am Soc Nephrol 9, 827–836 (1998)). During the last 4 hours, 2 uCi of $^3$H-thymidine (NEN-Dupont, Boston, Mass., USA) was added. Cells were then washed twice in PBS and lysed in 5N NaOH. $^3$H-thymidine incorporation of the cells was assessed in a liquid scintillation P counter (Beckman, Calif.).

RCC Tumor Model

6–8 weeks old NIH-3 nude beige xid mice (Harlan Sprague Dawley, Indiana, USA) and nude mice (Harlan Sprague Dawley) were injected subcutaneously in the right flank with 3 million 786-O cells in a 100 μl volume. Tumors appeared approximately 2 weeks after implantation. Tumor size was measured using calipers and tumor volume was calculated using the formula: volume=width/2× length/2. Tumor volume ranged from 150 to 200 mm$^3$. The animals were randomized into two groups with four mice each with comparable tumor size. Mice were then injected intraperitoneally with 100 μg monoclonal anti-TGFβ1, -β2, -β3 antibody (same antibody used in vitro and described above) or control nonspecific IgG (Sigma), on alternate days. When treatment was terminated, animals were sacrificed and tumors from each mouse removed and divided in two pieces: one was fixed in 10% formalin, paraffin embedded; the other was cryopreserved in OCT. The paraffin embedded specimens were stained with hematoxylin/eosin and Masson's trichrome stain and evaluated by light microscopy.

Immunohistochemistry

Factor VIII Staining/Microvessel Count

6 μm-thick sections from cryopreserved tumor specimens were stained for endothelial cells using Factor VIII antibody (Dako) with the use of a standard immunoperoxidase technique described previously (Cohen, H. T., Bossone, S. A., Zhu, G., McDonald, G. A. & Sukhatme, V. P., *J Biol Chem* 272, 2901–2913 (1997)). Microvessel count was done as assessed by the method of Delahunt, et al. (Delahunt, B., Bethwaite, P. B. & Thornton, A., *Br J Urol* 80, 401–404 (1997)). After the area of highest neovascularization was identified under low power (10×), individual microvessels were counted on 4 adjacent high power fields (40×) and the mean microvessel count was determined. Any area showing positive staining for Factor VIII was considered a countable vessel, whether or not a distinct lumen was visible. In the tumors where the microvasculature formed a dense network, each distinct branch was interpreted as a single vessel.

Proliferation Index/Apoptotic Index

Apotag plus in-situ apoptosis detection kit (Oncor, Gaithersburg, Md., USA) was used for measuring apoptotic index in paraffin sections of tumors and manufacturer's instructions were followed. Proliferative index was determined by using a monoclonal antibody against Ki 67, Clone MIB-I (Immunotech, Westbrook, Nebr., USA) on paraffin sections of tumors followed by standard immunoperoxidase technique. For both the indices, areas of the highest cellular staining were selected and 4 fields (each 0.65 mm$^3$) were studied. For each field the number of positive and negative staining tumor cells was quantified. These were combined to create a percentage of positive cells per unit area (2.6 mm$^3$).

Example 2

VHL but Not Mutant VHL Suppresses Endogenous TGF-β1 mRNA and Protein Levels in Stably Transfected RCC Cell Lines Several candidate genes are known to be upregulated in RCCs (VEGF, TGF-α, IL-6, EGF-receptor, and TGF-β1) were analysed by northern blot in 786-O RCC cell lines. 786-O RCC cells, derived from a patient with sporadic metastatic clear cell renal carcinoma, lack wild type pVHL (Iliopoulos, O., Kibel, A., Gray, S. & Kaelin, W. G., Jr., *Nat Med* 1, 822–826 (1995)). Strikingly, TGF-β1 mRNA levels were repressed about 4 fold in 786-O RCC cell lines stably transfected with wt-VHL (786-O HAVHL) compared to levels in the same cell lines transfected with an empty vector (786-O Neo) or transfected with a mutant VHL lacking a 116–213 (786-O HA ΔVHL) (FIG. 1A). To address the possibility of clonal variation, the findings in wild type 786-O cells and in 786-O Flag VHL cells were confirmed (FIG. 1A). Levels of protein expression from the stably transfected constructs were assessed by Western blot (FIG. 1B). ELISA confirmed that VHL transfected cells secreted about 3–4 fold less latent and active TGF-β1 protein in the culture supernatant (FIG. 1C). These data indicate that both TGF-β1 mRNA and protein are repressed by pVHL, indicating that TGF-β1 mRNA is a target for pVHL.

Example 3

TGF-β1 Is Regulated by pVHL at the Post-transcriptional Level

TGF-β1 is regulated by a number of different factors including phorbol esters, estrogens, retinoic acid, steroids and by itself (Roberts, A. B., *Miner Electrolyte Metab* 24, 111–119 (1998)). The regulation of TGF-β1 expression occurs both at transcriptional and post-transcriptional levels. Nuclear run-on in vitro experiments showed that reintroduction of wt-VHL in 786-O cells did not alter the transcription of TGF-β1 (FIG. 2A).

Nuclei from 786-O Neo, 786-HAVHL and from 786-O HAΔHL were isolated and nuclear run-on assays were performed in the presence of $^{32}$P-UTP for 30 min. The nascent $^{32}$P-labeled transcripts were hybridized to slots of filterbound TGF-β1, actin and GAPDH cDNA fragments. A control experiment with the addition of α-amanitin in the in vitro transcription assay confirmed that the detected transcripts were produced by RNA pol II. The filters were scanned and radioactivity measured on a Molecular Dynamics Phosphorimager. The transcription rate of TGF-β1 was normalized to the transcription rate of GAPDH within each experiment. The relative TGF-β1 transcription rate was 94.35 in the VHL expressing cells and 103.88 in the ΔVHL expressing cells, compared to an arbitrary 100 value in the Neo transfected cells (not statistically different).

Similarly, mutant VHL did not alter the transcription of the TGF-β1 gene (FIG. 2A). Experiments performed in the presence of α-amanitin showed inhibition of TGF-β1 transcription, indicating the specificity of the experimental conditions (FIG. 2A). A shorter TGF-β1 probe (a 700 bp in the 5' untranslated region) gave similar results. These nuclear run-on data suggest that the regulation of TGF-β1 by VHL is predominantly post-transcriptional, e.g. at the level of RNA splicing, nuclear export, or mRNA stability.

Figure 2B:
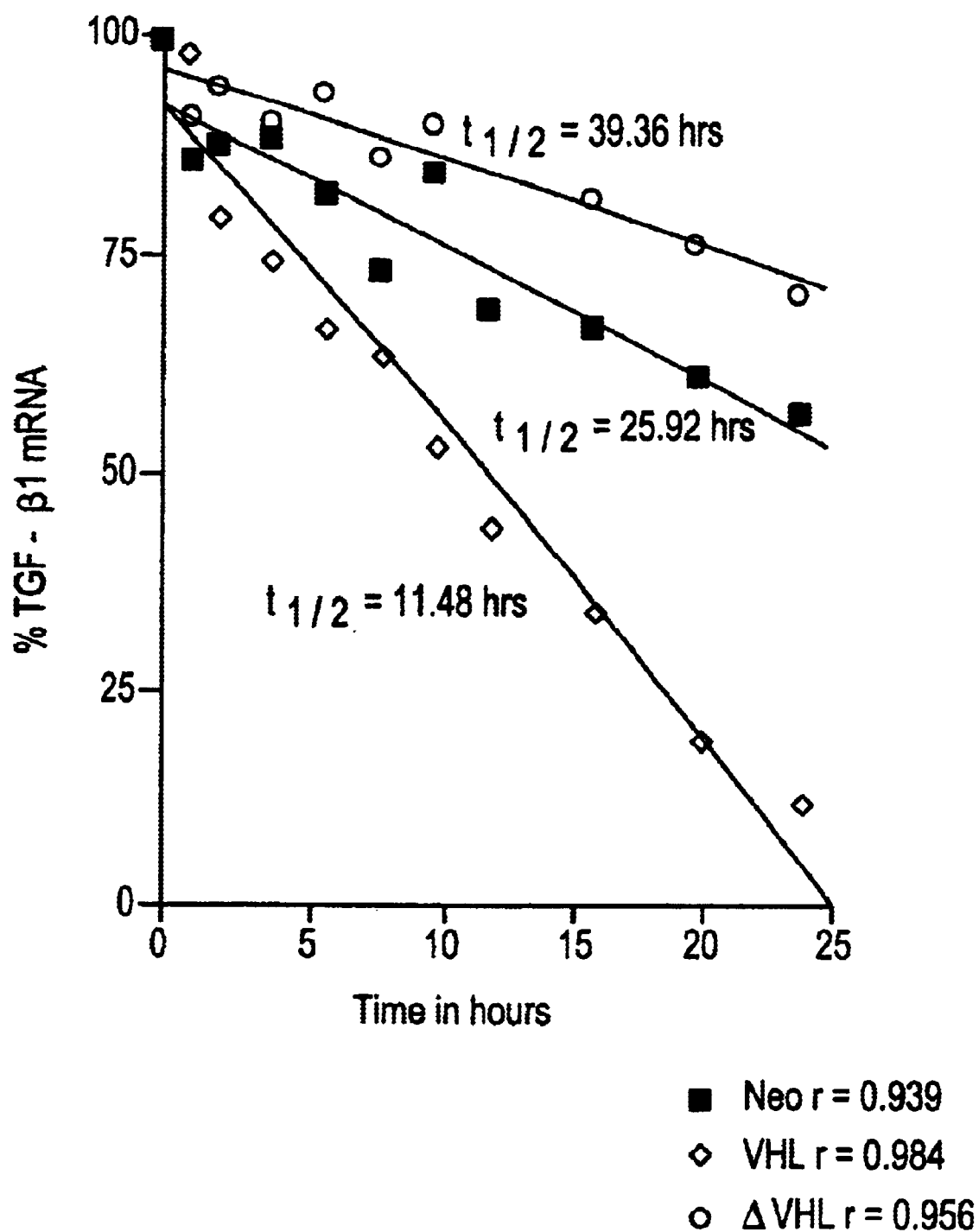
FIG. 2B is a graph showing the results of an experiment demonstrating that pVHL decreases the half-life of endogenous TGF-β1 message in stably transfected cells.

TGF-β mRNA stability in 786-O Neo, 786-O HAVHL and 786-O HA ΔVHL cells was also studied by measuring the decay of TGF-β1 mRNA in the presence of the transcriptional inhibitor Actinomycin-D. Subconfluent 786-O cells were incubated with Actinomycin-D (5 μg/ml) for various time points from 0–24 hrs. Total RNA was isolated and analysed by Northern blot hybridization with $^{32}$P-labeled TGF-β1. TGF-β1 message was quantitated by densitometry, normalized to 28S RNA and was plotted in a graph against time. Linear regression analysis indicated that the half-life of TGF-β1 was 25.92 hours in 786-O Neo cells, 39.36 hours in 786-O ΔVHL cells, and 11.48 hours in 786-O VHL cells. Results are the mean of 4 independent experiments and the regression coefficients (r) are shown. TGF-β1 mRNA half life was 11.48 hours in VHL transfected cells compared to 39.36 hours in mutant VHL transfected cells and 25.92 in empty vector transfected cells (FIG. 2B). Proof that Actinomycin-D was active during the early time points of the experiments came from probing the blots with a c-myc probe: the signal fell dramatically and was undetectable at 2 hours. These results suggest that pVHL destabilizes TGF-β1 mRNA.

Example 4

Figure 3B:
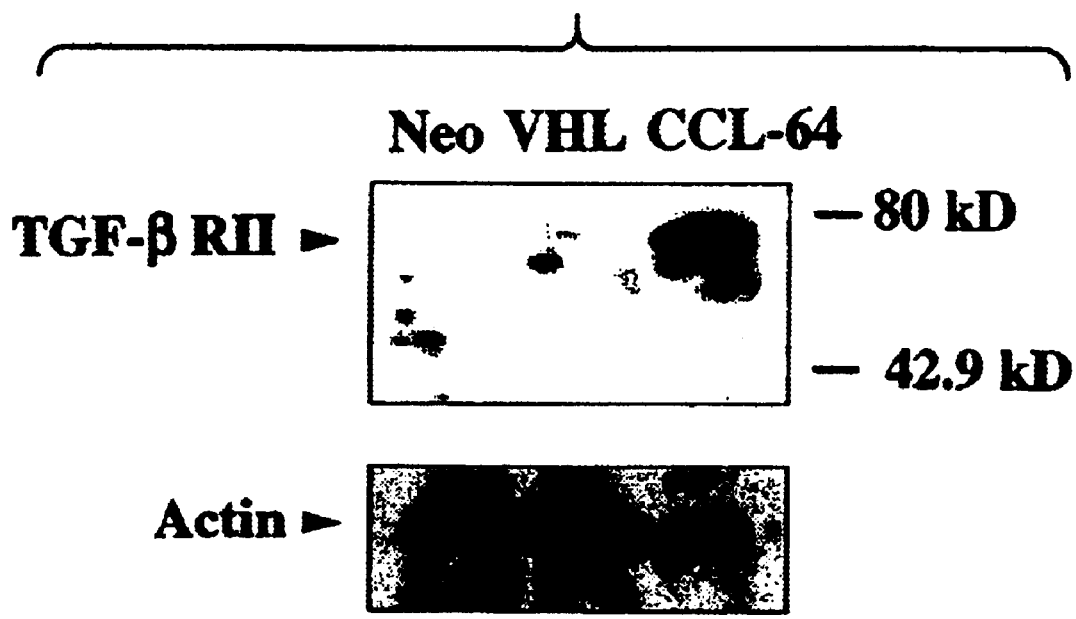
FIG. 3B is a photograph of Western blot analysis of TGF-β1 Type II receptor protein expression in RCC cells. Lysates from mink lung epithelial cells (CCL-64) which express functional TGF-β1 receptors was loaded as a positive control. Bottom panel shows the same blot reprobed with an actin antibody to compare loading and transfer.

786-O RCC Cells are Unresponsive to Exogenous TGF-β1 In Vitro and Lack Functional TGF-β Type II Receptor TGF-β1 binds with high affinity to the type II receptor. This binding is followed by recruitment of the type I receptor and subsequent intracellular signal transduction (Norgaard, P., Hougaard, S., Poulsen, H. S. & Spang-Thomsen, M., *Cancer Treat Rev* 21, 367–403 (1995)). It was first determined whether the RCC cell lines were growth responsive to exogenous TGF-β1. The growth of 786-O cells was unaffected by exogenous TGF-β1 at 1 ng/ml and 10 ng/ml (FIG. 3A). In addition, neutralizing antibody against TGF-β (used later in vivo) did not have any effect. As controls, mink lung epithelial cells (CCL-64) which have functional TGF-β receptors were found to be growth responsive to TGF-β1 and neutralizing antibody against TGF-β reversed the TGF-β1 induced growth suppression (FIG. 3A). The expression of TGF-β type 11 receptor protein in 786-O cells was also determined. Western blot analysis revealed no TGF-β type II receptor protein in 786-O Neo and 786-O HAVHL cells. Mink lung epithelial cells expressing functional TGF-β type I and II receptors were used as a positive control (FIG. 3B). These data suggest that the loss of type II receptor expression in 786-O cells is responsible for their unresponsiveness to TGF-β1 in vitro.

Example 5

Neutralizing Antibody Against TGF-β Inhibits Angiogenesis and RCC Tumor Growth in Athymic Mice To assess the biological significance of elevated TGF-β1 in RCCs, a xenograft athymic mouse model was used, since there is no syngeneic model for VHL-associated RCCs. Because TGF-β affects T-cell and NK cell activity, 786-O RCC cells were injected subcutaneously in the thigh region of nude beige xid (T, B and NK cell deficient) mice and the tumors were allowed to grow to 150–200 mm$^3$. 100 µg of the TGF-β monoclonal antibody (utilized earlier in FIG. 3A) or a control antibody was injected intraperitoneally on alternate days for 5 doses. Animals treated with TGF-β antibody showed a striking difference in tumor size when compared to controls (FIG. 4A) after 10 days. Interestingly, one of the four tumors in the treated group regressed to a small nodule of <50 mm$^3$. At the end of the experiment, the mice were sacrificed and the tumors examined histopathologically. There was no difference between treated and control groups on H & E stain (no infiltrating cells noted) and on Masson's trichrome stain. Areas of patchy necrosis in the rapidly growing control tumors were noted.

Figures 3, 4B:
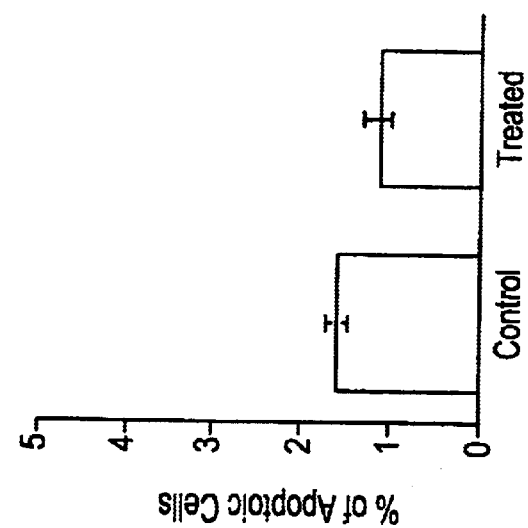
FIGS. 4B-1, 4B-2 and 4B-3 are a set of three histograms showing the results of an experiment where histological sections of tumors from TGF-β1 antibody treated and control antibody treated specimens were stained for Factor VIII (microvessel count), Ki-67 (proliferative index) and assessed for apoptosis (apoptotic index). The differences (*) between treated and control tumors were statistically significant (p<0.05) for microvessel count FIG. 4B-1 and proliferation index FIG. 4B-2, but not for apoptotic index FIG. 4B-3.
Figures 2, 4B:
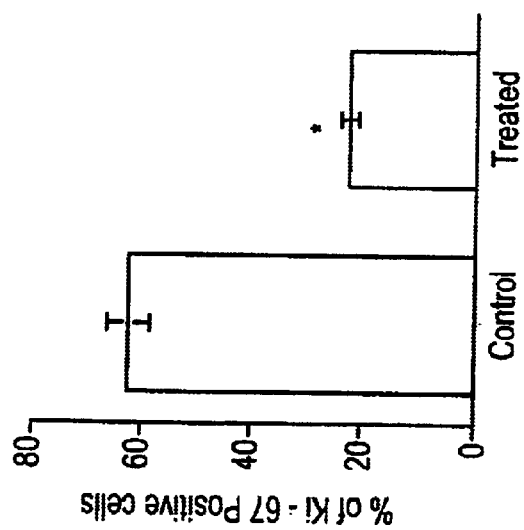
Figures 1, 4B:
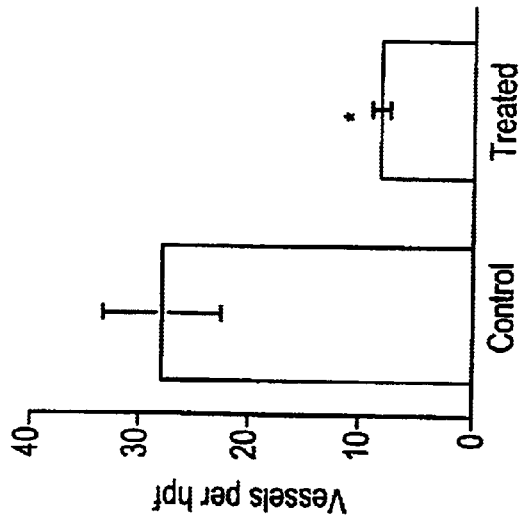
Figure 4C:
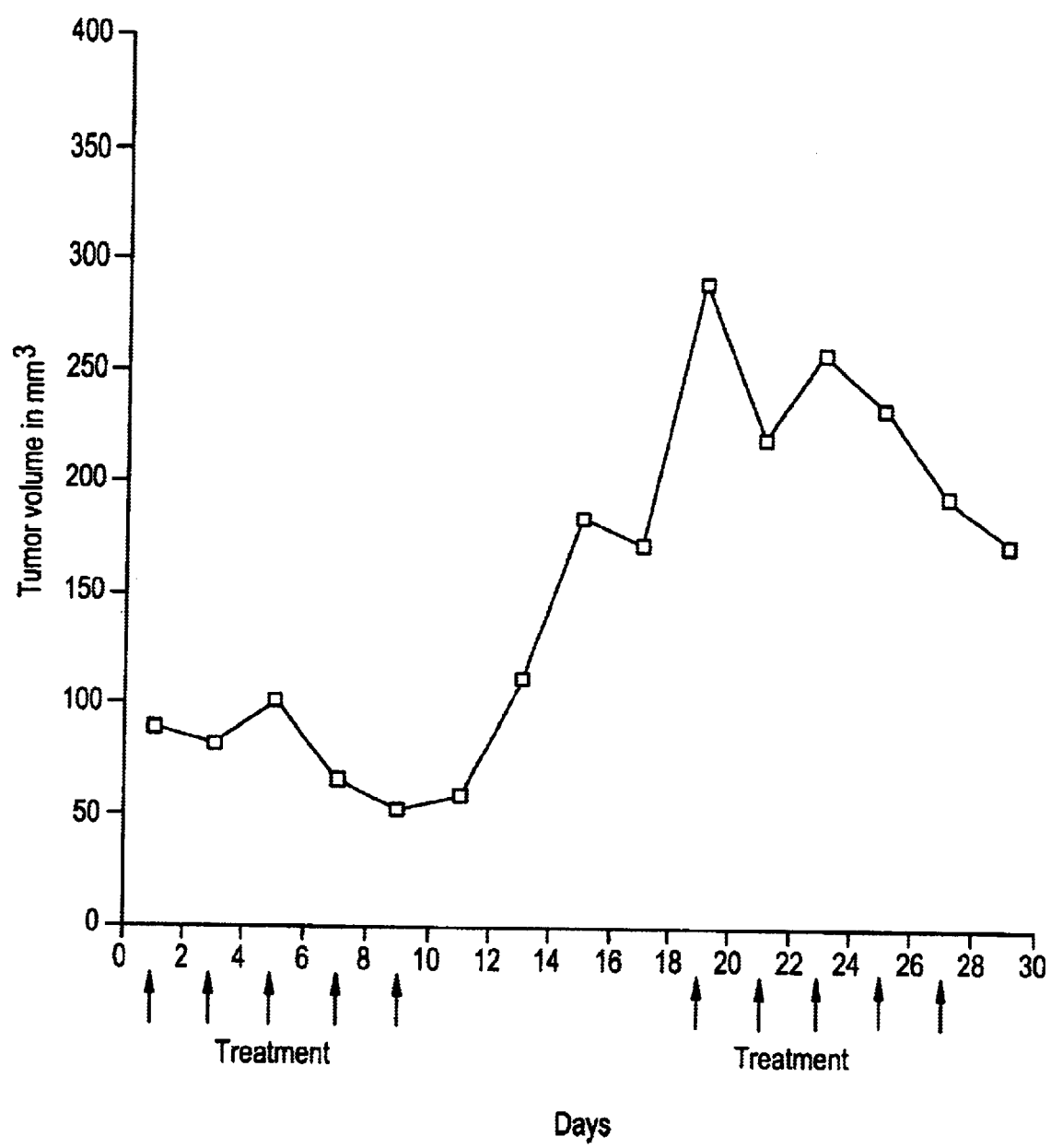
FIG. 4C is a graph showing the results of cyclical therapy with TGF-β1 antibody. When the tumor volume was approximately 100 mm$^3$, therapy was started with TGF-β antibody (n=2) or control antibody (n=2) on alternate days (days 1–9) as shown by arrows. Therapy was then stopped and re-started from days (19–27), as shown by arrows. Tumors were measured on alternate days. Each time point represent the average from 2 mice. The tumor size of the two control mice were 90 mm$^3$ (day 1), 467 mm$^3$ (day 13), and 1030 mm$^3$ (day 29) (data not shown in the graph, since it would be off-scale).

Importantly, Factor VIII staining showed a 3–4 fold decrease in the number of microvessels in the treated group (FIGS. 4B and 4C). Furthermore the proliferative index of the treated group was 3 fold lower than in the controls with no change in the apoptotic index (FIG. 4). Experiments repeated in athymic nude (nu/nu) mice (T cell deficient, but with normal NK activity; n=4 controls and 4 treated) gave very similar results, including one tumor regression. These data suggest that the primary mechanism of tumor suppression through the use of TGF-β neutralizing antibody is by inhibiting angiogenesis.

To assess whether tumor cells would develop resistance to TGF-β antibody treatment and whether larger tumors (250–300 mm$^3$) could be treated with the same dose, a separate experiment was conducted. As before, therapy with TGF-β antibody (2 animals) or control Ab (2 animals) was stopped after 10 days (FIG. 4D). Both tumors regressed in the treated group over this time period, but regrew rapidly upon cessation of therapy. Therapy was reinstituted when the mean tumor size was 280 mm$^3$, and tumor growth was again suppressed with a second course of TGF-β antibody. Collectively, these data suggest that antagonizing TGF-β in vivo significantly inhibits RCC tumors in athymic mice, with regressions seen in four of ten mice treated. Moreover, these tumors do not develop resistance to this therapy, consistent with the microvessel count data suggesting inhibition of anglogenesis as the therapeutic mechanism involved.

All references, patents, and patent applications are incorporated herein by reference in their entirety. While this invention has been particularly shown and described with references to preferred embodiments thereof, it will be understood by those of ordinary skill in the art that various changes in form and details may be made therein without departing from the spirit and scope of the invention as defined by the appended claims.

What is claimed is:

1. A method of inhibiting a proliferative disease in a vertebrate, wherein the proliferative disease is characterized by cells that secrete endogenous TGF-β and the disease is further characterized by angiogenesis, comprising inhibiting endogenous TGF-β activity by contacting the proliferating cells with less than 5 mg of an anti-TGF-β antibody, resulting in the inhibition of endogenous TGF-β-mediated angiogenesis, thereby inhibiting the proliferative disease, wherein the proliferative disease is selected from the group consisting of benign tumors and malignant tumors, and wherein the proliferative disease is clear-cell renal carcinoma.

* * * * *